(12) United States Patent
Ramsey et al.

(10) Patent No.: US 10,996,212 B2
(45) Date of Patent: May 4, 2021

(54) DEVICES AND SYSTEMS WITH FLUIDIC NANOFUNNELS FOR PROCESSING SINGLE MOLECULES

(71) Applicant: The University of North Carolina at Chapel Hill, Chapel Hill, NC (US)

(72) Inventors: John Michael Ramsey, Chapel Hill, NC (US); Laurent Menard, Raleigh, NC (US); Jinsheng Zhou, Chapel Hill, NC (US); Michael Rubinstein, Chapel Hill, NC (US); Sergey Panyukov, Moscow (RU)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 487 days.

(21) Appl. No.: 15/969,267

(22) Filed: May 2, 2018

(65) Prior Publication Data

US 2018/0252697 A1 Sep. 6, 2018

Related U.S. Application Data

(62) Division of application No. 14/368,971, filed as application No. PCT/US2013/025078 on Feb. 7, 2013, now Pat. No. 9,989,515.

(Continued)

(51) Int. Cl.
*G01N 33/487* (2006.01)
*B01L 3/00* (2006.01)
(Continued)

(52) U.S. Cl.
CPC .. *G01N 33/48721* (2013.01); *B01L 3/502707* (2013.01); *B01L 3/502761* (2013.01);
(Continued)

(58) Field of Classification Search
CPC ....... B01L 2200/0663; B01L 3/502761; B01L 3/502707; B01L 2400/0421;
(Continued)

(56) References Cited

U.S. PATENT DOCUMENTS 5,296,116 A 3/1994 Guttman
5,498,392 A 3/1996 Wilding et al.
(Continued)

FOREIGN PATENT DOCUMENTS

JP 2003-166934 6/2003
JP 2005-102619 4/2005
(Continued)

OTHER PUBLICATIONS

Uba et al. "Nanogap Electrical Detection of Single Molecules Translocating Through a Nanochannel with Transverse Nanoelectrodes and Funnels Populated With an Array of Nanopillars" pp. 401-403, 15th International Conference on Miniaturized Systems for Chemistry and Life Sciences, Seattle, Washington, USA, Oct. 2-6, 2011.
(Continued)

*Primary Examiner* — Benjamin R Whatley
(74) *Attorney, Agent, or Firm* — Myers Bigel, P.A.

(57) ABSTRACT

Methods of forming a chip with fluidic channels include forming (e.g., milling) at least one nanofunnel with a wide end and a narrow end into a planar substrate, the nanofunnel having a length, with width and depth dimensions that both vary over its length and forming (e.g., milling) at least one nanochannel into the planar substrate at an interface adjacent the narrow end of the nanofunnel.

18 Claims, 19 Drawing Sheets

Related U.S. Application Data

(60) Provisional application No. 61/597,364, filed on Feb. 10, 2012.

(51) Int. Cl.
  *C12Q 1/68*         (2018.01)
  *G01N 33/543*       (2006.01)
  *B29C 59/16*        (2006.01)

(52) U.S. Cl.
  CPC ............... *B29C 59/16* (2013.01); *C12Q 1/68* (2013.01); *G01N 33/54366* (2013.01); *B01L 2200/0663* (2013.01); *B01L 2300/0858* (2013.01); *B01L 2300/0864* (2013.01); *B01L 2300/0896* (2013.01); *B01L 2400/0421* (2013.01)

(58) Field of Classification Search
  CPC ..... B01L 2300/0858; B01L 2300/0864; B01L 2300/0896; G01N 33/54366; G01N 33/48721; C12Q 1/68; B29C 59/16
  See application file for complete search history.

(56) References Cited

U.S. PATENT DOCUMENTS

| | | |
|---|---|---|
| 5,858,187 A | 1/1999 | Ramsey et al. |
| 5,872,010 A | 2/1999 | Karger et al. |
| 5,900,130 A | 5/1999 | Benvegnu et al. |
| 6,074,827 A | 6/2000 | Nelson et al. |
| 6,235,471 B1 | 5/2001 | Knapp et al. |
| 6,500,323 B1 | 12/2002 | Chow et al. |
| 6,524,456 B1 | 2/2003 | Ramsey et al. |
| 6,537,433 B1 | 3/2003 | Bryning et al. |
| 6,592,733 B1 | 7/2003 | Foley et al. |
| 6,790,671 B1 | 9/2004 | Austin et al. |
| 6,803,568 B2 | 10/2004 | Bousse et al. |
| 6,846,398 B1 | 1/2005 | Heller et al. |
| 6,994,826 B1 | 2/2006 | Hasselbrink et al. |
| 7,033,474 B1 | 4/2006 | Dubrow et al. |
| 7,160,423 B2 | 1/2007 | Chien et al. |
| 7,229,540 B2 | 6/2007 | Okamoto et al. |
| 7,465,381 B2 | 12/2008 | Lopez et al. |
| 7,670,770 B2 | 3/2010 | Chou et al. |
| 7,744,762 B2 | 6/2010 | Lazar |
| 7,960,105 B2 | 6/2011 | Schwartz et al. |
| 8,246,799 B2 | 8/2012 | Oliver et al. |
| 8,333,934 B2 | 12/2012 | Cao et al. |
| 8,691,588 B2 | 4/2014 | Park et al. |
| 8,722,327 B2 | 5/2014 | Cao et al. |
| 8,735,065 B2 | 5/2014 | Craighead et al. |
| 8,764,968 B2 | 7/2014 | Afzali-Ardakani et al. |
| 8,940,147 B1 | 1/2015 | Bartsch et al. |
| 9,061,901 B2 | 6/2015 | Cao et al. |
| 9,255,288 B2 | 2/2016 | Ramsey et al. |
| 9,618,479 B2 | 4/2017 | Ramsey et al. |
| 9,970,898 B2 | 5/2018 | Ramsey et al. |
| 10,571,428 B2 | 2/2020 | Ramsey et al. |
| 2002/0000516 A1 | 1/2002 | Schultz et al. |
| 2002/0061529 A1 | 5/2002 | Bridgham et al. |
| 2002/0072243 A1 | 6/2002 | Craighead et al. |
| 2002/0081744 A1 | 6/2002 | Chan et al. |
| 2002/0160365 A1 | 10/2002 | O'Brien |
| 2002/0190204 A1 | 12/2002 | Hofstadler et al. |
| 2002/0197603 A1 | 12/2002 | Chow et al. |
| 2003/0136679 A1 | 7/2003 | Bohn et al. |
| 2003/0146377 A1 | 8/2003 | Miller et al. |
| 2004/0033515 A1 | 2/2004 | Cao et al. |
| 2004/0166504 A1 | 8/2004 | Rossier et al. |
| 2005/0023156 A1 | 2/2005 | Ramsey et al. |
| 2005/0082204 A1 | 4/2005 | Schwartz et al. |
| 2005/0103713 A1 | 5/2005 | Ramsey et al. |
| 2005/0196746 A1 | 9/2005 | Xu et al. |
| 2006/0084078 A1 | 4/2006 | Zhao |
| 2006/0169587 A1 | 8/2006 | Lopez et al. |
| 2006/0240573 A1 | 10/2006 | Kao et al. |
| 2006/0275778 A1 | 12/2006 | Wu et al. |
| 2006/0278879 A1 | 12/2006 | Busta |
| 2007/0057179 A1 | 3/2007 | Bousse et al. |
| 2007/0145263 A1 | 6/2007 | Weng |
| 2007/0192911 A1 | 8/2007 | Jin et al. |
| 2008/0057192 A1 | 3/2008 | Faguet |
| 2008/0242556 A1* | 10/2008 | Cao ................... B01L 3/50273 506/9 |
| 2009/0023146 A1 | 1/2009 | Harnack et al. |
| 2009/0111115 A1 | 4/2009 | Drmanac et al. |
| 2009/0115094 A1 | 5/2009 | Chou et al. |
| 2009/0136682 A1 | 5/2009 | Branton et al. |
| 2009/0305273 A1 | 12/2009 | Cao et al. |
| 2010/0029508 A1 | 2/2010 | Austin et al. |
| 2010/0029915 A1 | 2/2010 | Duthie et al. |
| 2010/0075428 A1 | 3/2010 | Wang et al. |
| 2010/0159462 A1 | 6/2010 | Takayama et al. |
| 2010/0267158 A1 | 10/2010 | Chou et al. |
| 2011/0036994 A1 | 2/2011 | Frayling |
| 2011/0155575 A1 | 6/2011 | Doraira j et al. |
| 2011/0201509 A1 | 8/2011 | Tegenfeldt et al. |
| 2011/0226623 A1 | 9/2011 | Timp et al. |
| 2011/0227558 A1 | 9/2011 | Mannion et al. |
| 2011/0296903 A1 | 12/2011 | Cao et al. |
| 2011/0308949 A1 | 12/2011 | Afzali-Ardakani et al. |
| 2012/0193231 A1 | 8/2012 | Afzali-Ardakani et al. |
| 2012/0196376 A1 | 8/2012 | Park et al. |
| 2013/0068618 A1 | 3/2013 | Harrer et al. |
| 2013/0195723 A1 | 8/2013 | Ramsey et al. |
| 2013/0224736 A1 | 8/2013 | Marie et al. |
| 2013/0224763 A1 | 8/2013 | Kimura |
| 2014/0194313 A1 | 7/2014 | Craighead et al. |
| 2014/0194314 A1 | 7/2014 | Walsworth et al. |
| 2014/0197105 A1 | 7/2014 | DiBiasio et al. |
| 2014/0238856 A1 | 8/2014 | Ramsey et al. |
| 2014/0272958 A1 | 9/2014 | Ramsey et al. |
| 2015/0008124 A1 | 1/2015 | Oliver |
| 2016/0024569 A1 | 1/2016 | Ramsey et al. |
| 2017/0175181 A1 | 6/2017 | Ramsey et al. |

FOREIGN PATENT DOCUMENTS

| | | |
|---|---|---|
| JP | 2005241255 A | 9/2005 |
| JP | 2007-149861 | 6/2007 |
| WO | WO 96/04547 A1 | 2/1996 |
| WO | WO 00/002038 A1 | 1/2000 |
| WO | WO 01/13088 A1 | 2/2001 |
| WO | WO 03/025540 A2 | 3/2003 |
| WO | WO 2007/011622 A2 | 1/2007 |
| WO | WO 2008/079169 A2 | 7/2008 |
| WO | WO 2008/132734 A2 | 11/2008 |
| WO | WO 2009/030953 A1 | 3/2009 |
| WO | WO 2009/052214 A2 | 4/2009 |
| WO | WO 2009/120642 A1 | 10/2009 |
| WO | WO 2012/040098 A2 | 3/2012 |
| WO | WO 2012/055415 A1 | 5/2012 |
| WO | WO 2012/170560 A2 | 12/2012 |
| WO | WO 2013/039778 A2 | 3/2013 |
| WO | WO 2013/088098 A2 | 6/2013 |
| WO | WO 2013/119765 A1 | 8/2013 |
| WO | WO 2013/176767 A1 | 11/2013 |
| WO | WO 2013/191908 A1 | 12/2013 |

OTHER PUBLICATIONS

Wu et al. "Complete plastic nanofluidic devices for DNA analysis via direct imprinting with polymer stamps" Lab on a Chip, 11(17):2984-2989 (2011).

Abgrall et al. "Nanofluidic Devices and Their Applications" *Analytical Chemistry* 80:2326-2341 (2008).

Al et al. "Field Effect Regulation of DNA Translocation through a Nanopore" *Analytical Chemistry* 82(19):8217-8225 (2010).

Alkan et al. "Genome structural variation discovery and genotyping" *Nat. Rev. Genet.* 12:363-376 (2011).

(56) References Cited

OTHER PUBLICATIONS

Allison et al. "Direct atomic force microscope imaging of EcoRI endonuclease site specifically bound to plasmid DNA molecules" *Proc. Natl. Acad. Sci. USA*, 93:8826-8829 (1996).
Apel et al. "Diode-like single-ion track membrane prepared by electro☐stopping" *Nucl. Instrum. Methods Phys. Res.*, Sect. B, 2001, 184, 337-346.
Baday et al., "Multicolor super-resolution DNA imaging for genetic analysis", *Nano Lett.*, 2012, vol. 12, pp. 3861-3866.
Balducci et al. "Double-Stranded DNA Diffusion in Slitlike Nanochannels" *Macromolecules* 39:6273-6281 (2006).
Balducci et al. "Conformational preconditioning by electrophoresis of DNA through a finite obstacle array", *Macromolecules*, 2008, vol. 41, pp. 5485-5492.
Brochard et al. "Dynamics of confined polymer chains", J. Chem. Phys., Jul. 1977, vol. 67, pp. 52-56.
Brochard-Wyart et al. "Dynamics of Taut DNA chains", *Europhys. Lett.*, 1999, vol. 47(2), pp. 171-174.
Campbell et al. "Electrophoretic manipulation of single DNA molecules in nanofabricated capillaries", *Lab Chip*, 2004, 4:225-229.
Cao et al. "Fabrication of 10 nm enclosed nanofluidic channels", *Applied Physics Letters*, vol. 81, No. 1, Jul. 2002, pp. 174-176.
Cao et al. "Gradient nanostructures for interfacing microfluidics and nanofluidics", *Appl. Phys. Lett.*, Oct. 14, 2002; vol. 81, No. 16, pp. 3058-3060.
Chantiwas et al., "Flexible fabrication and applications of polymer nanochannels and nanoslits", *Chem. Soc. Rev.*, 2011, vol. 40, pp. 3677-3702.
Chou et al. "A microfabricated device for sizing and sorting DNA molecules", *Proc. Natl. Acad. Sci.*, 1999, vol. 96, pp. 11-13.
Cipriany et al. "Single molecule epigenetic analysis in a nanofluidic channel", Anal. Chem., Mar. 15, 2010, vol. 82, No. 6, pp. 2480-2487.
Craddock et al., "Genome-wide association study of CNVs in 16,000 cases of eight common diseases and 3,000 shared controls", *Nature*, 2010, vol. 464, pp. 713-720.
Craighead et al. "Future lab-on-a-chip technologies for interrogating individual molecules" Nature 2006, 442, 387.
Cross et al. "Size-dependent DNA mobility in nanochannels", *Journal of Applied Physics*, 2007, vol. 102, pp. 024701-1-024701-5.
Cui, S.T., "Counterion-Hopping along the Backbone of Single-Stranded DNA in Nanometer Pores: A Mechanism for Current Conduction", *Physical Review Letters*, 2007, vol. 98, pp. 138101-1-138101-4.
Das et al., "Single molecule linear analysis of DNA in nano-channel labeled with sequence specific fluorescent probes", *Nucl. Acids Res.*, 2010, vol. 38, e177, 8 pages.
Dimalanta et al., "A microfluidic system for large DNA molecule arrays", *Anal. Chem.*, 2004, vol. 76, pp. 5293-5301.
Douville et al., "DNA linearization through confinement in nanofluidic channels", *Anal Bioanal Chem.*, 2008, vol. 391, pp. 2395-2409.
Duke et al. "Microchips for Sorting DNA" pp. 11-26 (1997).
Eijkel et al. "Nanofluidics: what is it and what can we expect from it?" Microfluid. Nanofluid. 2005, 1, 249.
Extended European Search Report corresponding to European Patent Application No. 13746055.6 (8 pages) (dated Aug. 28, 2015).
Fan et al. "DNA Translocation in Inorganic Nanotubes", *Nano Letters* 5(9):1633-1637 (2005).
Fischbein et al. "Sub-10 nm Device Fabrication in a Transmission Electron Microscope" Nano Letters 2007, vol. 7, 1329.
Foquet et al., "DNA fragment sizing by single molecule detection in submicrometer-sized closed fluidic channels", *Anal. Chem.*, 2002, vol. 74, pp. 1415-1422.
Freitag et al., "Meandering nanochannels for imaging of ultra-long DNA molecules", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, pp. 1758-1760.

Gierak et al. "Sub-5 nm FIB direct patterning of nanodevices", *Microelectronic Engineering*, 2007, vol. 84, pp. 779-783.
Gierhart et al. "Nanopore with transverse nanoelectrodes for electrical characterization and sequencing of DNA" Sens. and Actuators B 2008, 132, 593.
Han et al., "Prediction of nanopattern topography using two-dimensional focused ion beam milling with beam irradiation intervals", *Microelectronic Engineering*, 2010, vol. 87, pp. 1-9.
Han et al., "Separation of long DNA molecules in a microfabricated entropic trap Array", *Science*, May 12, 2000; vol. 288, No. 5468, pp. 1026-1029.
Haneveld et al., "Wet anisotropic etching for fluidic 1D nanochannels", *J. Micromech. Microeng.*, 2003, vol. 13, pp. S62-S66.
Holzer et al., "Three-dimensional analysis of porous $BaTiO_3$ ceramics using FIB nanotomography", *Journal of Microscopy*, vol. 216, Pt. 1, Oct. 2004, pp. 84-95.
Huh et al., "Tuneable elastomeric nanochannels for nanofluidic manipulation", *Nature Materials*, vol. 6, Jun. 2007, pp. 424-428.
International Preliminary Report on Patentability Corresponding to International Application No. PCT/US2013/025078 (8 pages) (dated Aug. 12, 2014).
International Search Report and the Written Opinion of the International Searching Authority corresponding to International Patent Application No. PCT/US2013/025078 (12 pages) (dated May 15, 2013).
Jo et al. "A single-molecule barcoding system using nanoslits for DNA analysis", *Proc. Natl. Acad. Sci.*, vol. 104, No. 8, pp. 2673-2678 (2007).
Jo et al. "Elongation and migration of single DNA molecules in microchannels using oscillatory shear flows" *Lab on a Chip* 9:2348-2355 (2009).
Kasianowicz et al. "Nanoscopic Porous Sensors" *Annual Review of Analytical Chemistry* 1:737-766 (2008).
Kim et al., "A highly annotated whole-genome sequence of a Korean individual", *Nature*, 2009, vol. 460, pp. 1011-1015.
Kim et al., "Design and numerical simulation of a DNA electrophoretic stretching device", *Lab Chip*, 2007, vol. 7, pp. 213-215.
Kovarik et al., "Nanofluidics in Lab-on-a-Chip Devices", *Anal. Chem.*, 2009, vol. 81, No. 17, pp. 7133-7140.
Kumar et al., "Origin of translocation barriers for polyelectrolyte chains", J. Chem. Phys. 2009, vol. 131, pp. 194903-1-194903-18.
Lagerqvist et al. "Fast DNA Sequencing via Transverse Electronic Transport", *Nano Letters*, 2006, vol. 6, No. 4, pp. 779-782.
Lam et al., "Genome mapping on nanochannel arrays for structural variation analysis and sequence assembly", *Nat. Biotech.*, Aug. 2012, vol. 30, No. 8, pp. 771-776.
Larson et al., "Single DNA molecule stretching in sudden mixed shear and elongational microflows", *Lab Chip*, 2006, vol. 6, Issue 9, pp. 1187-1199.
Lerman et al. "Why Does the Electrophoretic Mobility of DNA in Gels Vary with the Length of the Molecule?", *Biopolymers*, 1982, vol. 21, pp. 995-997.
Lerman et al., Communications to the Editor "Why Does the Electrophoretic Mobility of DNA in Gels Vary with the Length of the Molecule?" Biopolymers 1982, 21, 995-997.
Levy et al. "Entropic Unfolding of DNA Molecules in Nanofluidic Channels" Nano Letters, 2008, 8, 3839.
Levy et al., "DNA manipulation, sorting, and mapping in nanofluidic systems", Chem Soc Rev 2010; vol. 39, Issue 3, pp. 1133-1152.
Li et al. "Sacrificial polymers for nanofluidic channels in biological applications" Nanotechnology 2003, 14, 578.
Li et al., "Focused ion beam fabrication of silicon print masters", *Nanotechnology*, 2003, vol. 14, pp. 220-223.
Liang et al. "Single Sub-20 nm Wide, Centimeter-Long Nanofluidic Channel Fabricated by Novel Nanoimprint Mold Fabrication and Direct Imprinting", Nano Letters, 2007, vol. 7, 3774.
Liang et al., "Nanogap detector inside nanofluidic channel for fast real-time label-free DNA analysis", Nano Letters, 2008, vol. 8, No. 5, pp. 1472-1476.
Lim et al., "DNA methylation profiling in nanochannels", *Biomicrofluidics*, 2011, vol. 5, 034106, 9 pages.
Lugstein et al., "FIB processing of silicon in the nanoscale regime", *Applied Physics A*, 2003, vol. 76, pp. 545-548.

(56) References Cited

OTHER PUBLICATIONS

Maleki et al., "A nanofluidic channel with embedded transverse nanoelectrodes", *Nanotechnology*, 2009, vol. 20:105302, pp. 1-6.
Mannion et al., "Conformational analysis of single DNA molecules undergoing entropically induced motion in nanochannels", *Biophys. J.*, 2006, vol. 90, pp. 4538-4545.
Mao et al. "Fabrication and characterization of 20 nm planar nanofluidic channels by glass-glass and glass-silicon bonding" Lab Chip 2005, 5, 837.
Marie et al. "Nanofluidic devices towards single DNA molecule sequence mapping" *Journal of Biophotonics* 5(8-9):673-686 (2012).
Mark et al., "Microfluidic lab-on-a-chip platforms: requirements, characteristics and applications", *Chem. Soc. Rev.*, 2010, vol. 39, pp. 1153-1182.
McCarroll et al., "Copy-number variation and association studies of human disease", *Nat. Genet.*, 2007, vol. 39, pp. S37-S42.
McCarthy et al., "Microduplications of 16p11.2 are associated with schizophrenia", *Nat. Genet.*, 2009, vol. 41, No. 11, pp. 1223-1227.
Menard et al., "A Device for Performing Lateral Conductance Measurements on Individual Double-Stranded DNA Molecules", *ACS Nano*, 2012, vol. 6(10), pp. 9087-9094.
Menard et al., "Analysis of Single DNA Molecules Translocating Through Nanochannels Fabricated in $SiO_2$", *Twelfth International Conference on Miniaturized Systems for Chemistry and Life Sciences*, Oct. 12-16, 2008, San Diego, California, 4 pages.
Menard et al., "Electrokinetically-Driven Transport of DNA Through Focused Ion Beam Milled Nanofluidic Channels", *Anal. Chem.*, 2013, vol. 85, pp. 1146-1153.
Menard et al., "Fabrication of Sub-5 nm Nanochannels in Insulating Substrates Using Focused Ion Beam Milling", *Nano Letters*, 2011, vol. 11, No. 2, pp. 512-517.
Menard, Jr. et al., "DNA Transport Characteristics in Focused Beam-Milled Nanofluidic Devices", *2009 Annual Meeting of the American Electrophoresis Society (AES)*, Nov. 10, 2009, Retrieved from the internet at URL http://aiche.confex.com/aiche/2009/webprogram/Paaper160572.html.
Mijatovic et al., "Technologies for nanofluidic systems: top-down vs. bottom-up—a review", *Lab Chip*, 2005, vol. 5, pp. 492-500.
Mills et al., "Mapping copy number variation by population-scale genome sequencing", *Nature*, 2011, vol. 470, pp. 59-65.
Nakayama et al., "Stability and Schottky barrier of silicides: First-principles study", *Microelectronic Engineering*, 2009, vol. 86, pp. 1718-1721.
Nikoobakht, B., "A Scalable Platform for Integrating Horizontal Nanochannels with Known Registries to Microchannels", *Chem. Mater.*, 2009, vol. 21, pp. 27-32.
Office Action corresponding to Japanese Patent Application No. 2014-556651 (7 pages) (dated Dec. 27, 2016).
Orloff et al., "Fundamental limits to imaging resolution for focused ion beams", *Journal of Vacuum Science & Technology B*, Nov./Dec. 1996, vol. 14, No. 6, pp. 3759-3763.
Pang et al. "Fixed-Gap Tunnel Junction for Reading DNA Nucleotides" *ACS Nano* 8(12):11994-12003 (2014).
Perry et al., "Review of fabrication of nanochannels for single phase liquid flow" *Microfluid Nanofluid*, vol. 2:185-193 (2006).
Perry et al. "Ion transport in nanofluidic funnels", *ACS Nano* 4(7):3897-3902 (2010).
Persson et al. "Confinement spectroscopy: probing single DNA molecules with tapered nanochannels" *Nano Letters* 9(4):1382-1385 (2009).
Pinard et al., "Assessment of whole genome amplification-induced bias through high-throughput, massively parallel whole genome sequencing", *BMC Genomics*, 2006, vol. 7, 216, 21 pages.
Pinkel et al., "Comparative genomic hybridization", *Annu. Rev. Genomics Hum. Genet.*, 2005, vol. 6, pp. 331-354.
Pinto et al., "Functional impact of global rare copy number variation in autism spectrum disorders", *Nature*, 2010, vol. 466, pp. 368-372.
Randall et al., "Methods to electrophoretically stretch DNA: microcontractions, gels, and hybrid gel-microcontraction devices", *Lab Chip*, 2006, vol. 6, pp. 516-525.
Randolph et al., "Focused, Nanoscale Electron-Beam-Induced Deposition and Etching", *Critical Reviews in Solid State and Materials Sciences*, 2006, 31:3, pp. 55-89.
Reccius et al., "Conformation, length, and speed measurements of electrodynamically stretched DNA in nanochannels", *Biophys. J.*, Jul. 2008, vol. 95, pp. 273-286.
Reisner et al. "Statics and Dynamics of Single DNA Molecules Confined in Nanochannels", *Physical Review Letters*, vol. 94, pp. 196101-1-196101-4 (2005).
Reisner et al. "Nanoconfinement-Enhanced Conformational Response of Single DNA Molecules to Changes in Ionic Environment", *Physical Review Letters*, vol. 99, pp. 058302-1-058302-4 (2007).
Reisner et al. "Single-molecule denaturation mapping of DNA in nanofluidic channels" *Proceedings of the National Academy of Sciences* 107(30):13294-13299 (2010).
Reisner et al. "DNA confinement in nanochannels: physics and biological applications", *Rep. Prog. Phys.*, vol. 75, Issue 10, 106601, 35 pages (2012).
Riehn et al. "Restriction mapping in nanofluidic devices" *Proceedings of the National Academy of Sciences* 102(29):10012-10016 (2005).
Salieb-Beugelaar et al., "Electrophoretic separation of DNA in gels and nanostructures", *Lab Chip*, 2009, vol. 9, pp. 2508-2523.
Salieb-Beugelaar et al., "Field-Dependent DNA Mobility in 20 nm High Nanoslits", *Nano Letters*, Jul. 2008, vol. 8, No. 7, pp. 1785-1790.
Schoch, R.B., "Transport phenomena in nanofluidics", *Reviews of Modern Physics*, vol. 80, No. 3, Jul.-Sep. 2008, pp. 839-883.
Sebat et al., "Strong association of de novo copy number mutations with autism", *Science*, 2007, vol. 316, pp. 445-449.
Smeets et al. "Salt Dependence of Ion Transport and DNA Translocation through Solid State Nanopores" Nano Letters 2006, vol. 6, No. 1, 89.
Smith et al., "Overstretching B-DNA: The elastic response of individual double-stranded and single-stranded DNA molecules", *Science*, 1996, vol. 271, pp. 795-799.
So et al. "Inherently aligned microfluidic electrodes composed of liquid metal", Lab Chip, 2011, 11, 905-911.
Sorek et al., "Genome-wide experimental determination of barriers to horizontal gene transfer", *Science*, 2007, vol. 318, pp. 1449-1452.
Speicher et al., "Effect of genome-wide association studies, direct-to-consumer genetic testing, and high-speed sequencing technologies on predictive genetic counselling for cancer risk", *Lancet Oncol.*, Sep. 2010, vol. 11, pp. 890-898.
Stavis et al., "Nanofluidic structures with complex three-dimensional surfaces", *Nanotechnology*, 2009, vol. 20, Issue 16, 165302, 7 pages.
Stefansson et al., "Large recurrent microdeletions associated with schizophrenia", *Nature*, 2008, vol. 455, pp. 232-236.
Striemer et al., "Charge- and size-based separation of macromolecules using ultrathin silicon membranes", *Nature*, Feb. 15, 2007; vol. 445, pp. 749-753.
Strychalski et al., "Diffusion of DNA in Nanoslits", *Macromolecules*, 2008, vol. 41, pp. 7716-7721.
Strychalski et al. "Non-planar nanofluidic devices for single molecule analysis fabricated using nanoglassblowing" *Nanotechnology* 19(16):315301 (2008).
Taniguchi et al., Fabrication of the gating nanopore device, *Applied Physics Letters*, vol. 95, pp. 123701-1-123701-3 (2009).
Teague et al., "High-resolution human genome structure by single-molecule analysis", *Proc. Natl. Acad. Sci.*, vol. 107, pp. 10848-10853 (2010).
Tegenfeldt et al., "The dynamics of genomic-length DNA molecules in 100-nm Channels", *Proc. Natl. Acad. Sci.*, Jul. 27, 2004; vol. 101, No. 30, pp. 10979-10983.
Tong et al., "Silicon Nitride Nanosieve Membrane", *Nano Letters*, 2004, vol. 4, No. 2, pp. 283-287.
Topolancik et al., "Extraction and purification of genomic DNA via entrapment in an array of microposts", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, p. 1026-1028.

(56) References Cited

OTHER PUBLICATIONS

Treangen et al., "Repetitive DNA and next-generation sequencing: computational challenges and solutions", *Nat. Rev. Genet.*, 2011, vol. 13, pp. 36-46.
Tseng, A., "Recent developments in micromilling using focused ion beam technology", *J. Micromech. Microeng.*, 2004, vol. 14, pp. R15-R34.
Tsutsui et al. "Transverse Field Effects on DNA-Sized Particle Dynamics" Nano Letters 2009, vol. 9, No. 4, 1659.
Turner et al., "Confinement-induced entropic recoil of single DNA molecules in a nanofluidic structure", *Phys. Rev. Lett.*, 2002, vol. 88, 128103.
Utko et al., "Injection molded nanofluidic chips: Fabrication method and functional tests using single-molecule DNA experiments", *Lab Chip*, 2011, vol. 11, pp. 303-308.
Viero et al. "Hydrodynamic Manipulation of DNA in Nanopost Arrays: Unhooking Dynamics and Size Separation" *Small* 7(24):3508-3518 (2011).
Volkmuth et al. "DNA electrophoresis in microlithographic arrays", *Nature*, Aug. 13, 1992; vol. 358, pp. 600-602.
Wang et al. "Single-molecule studies of repressor-DNA interactions show long-range interactions" *PNAS* 102(28):9796-9801 (2005).
Wang et al. "Manipulating DNA molecules in nanofluidic channels", *Microfluid Nanofluid*, 2:85-88 (2006).
Wanunu, Meni "Nanopores: A journey towards DNA sequencing" *Physics of Life Reviews* 9:125-158 (2012).
Xu et al. "Wide-spectrum, ultrasensitive fluidic sensors with amplification from both fluidic circuits and metal oxide semiconductor field effect transistors" *Applied Physics Letters* vol. 91, pp. 013901-1-013901-3 (2007).
Yuan et al. "Electrokinetic transport and separations in fluidic nanochannels", *Electrophoresis* vol. 28, pp. 595-610 (2007).
Zangle et al., "Theory and experiments of concentration polarization and ion focusing at microchannel and nanochannel interfaces" *Chem. Soc. Rev.* 39:1014-1035 (2010).
Zhou et al. "A whole-genome shotgun optical map of Yersinia pestis strain KIM", *Appl. Environ. Microbiol.*, vol. 68, No. 12, pp. 6321-6331 (2002).
Zhou et al. "Whole-genome shotgun optical mapping of Rhodobacter sphaeroides strain 2.4.1 and its use for whole-genome shotgun sequence assembly", *Genome Res.*, vol. 13, pp. 2142-2151 (2003).
Zhou et al. "A single molecule system for whole genome analysis", *Perspectives in Bioanalysis, vol. 2, New High Throughput Technologies for DNA Sequencing and Genomics*; Mitchelson, K. R., Ed.; Elsevier: Amsterdam; pp. 265-300 (2007).
Zhou et al. "Transport and Sensing in Nanofluidic Devices" *Annual Review of Analytical Chemistry* 4:321-341 (2011).
Zhu et al. "Arrays of horizontally-oriented mini-reservoirs generate steady microfluidic flows for continuous perfusion cell culture and gradient generation" *The Analyst* 129:1026-1031 (2004).
Zwolak, M., "Electronic Signature of DNA Nucleotides via Transverse Transport", *Nano Letters*, 2005, vol. 5, No. 3, pp. 421-424.
EPO machine translation of the Description section of JP 2005-241255, patented Sep. 8, 2005, translation downloaded Dec. 15, 2020 (Year: 2005).
Evans, Christine E. "Direct On-Line Injection in Capillary Electrophoresis" Analytical Chemistry, 69:2952-2954 (1997).
Karlinsey, James M. "Sample introduction techniques for microchip electrophoresis: A review" Analytica Chimica Acta, 725:1-13 (2012).

\* cited by examiner

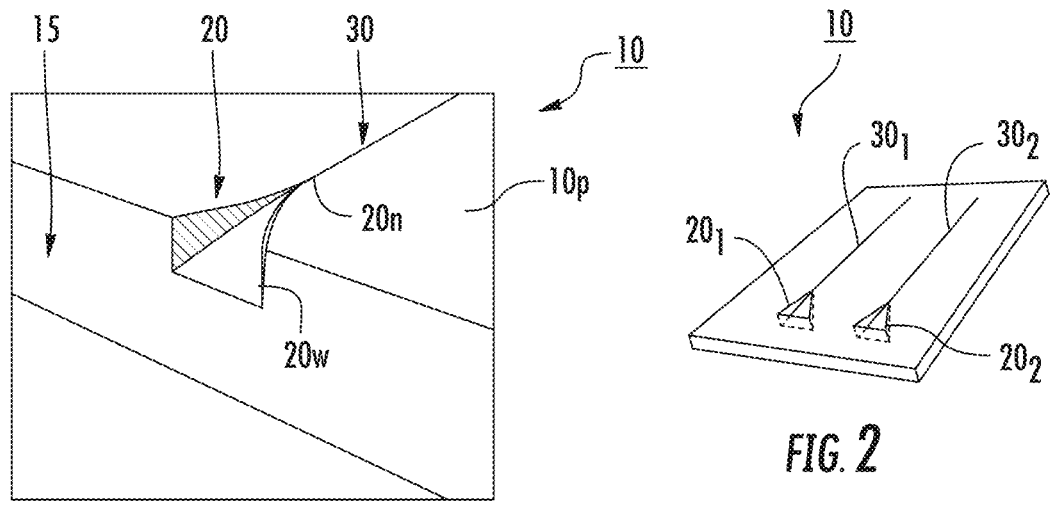
FIG. 1
FIG. 2
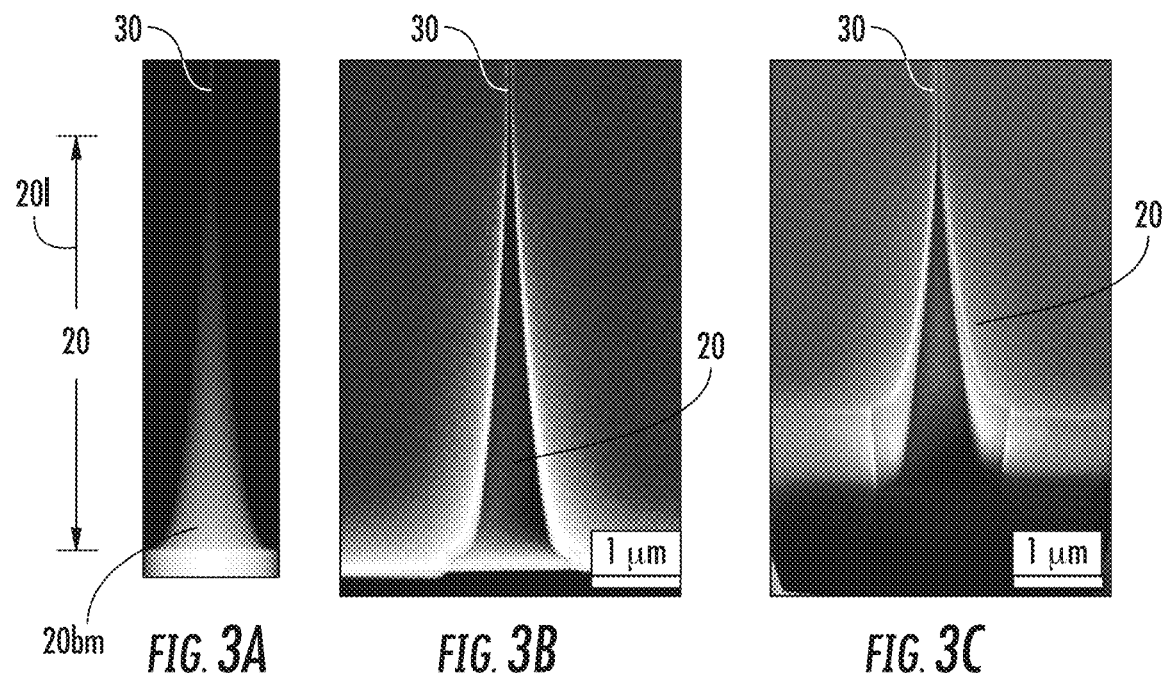
FIG. 3A
FIG. 3B
FIG. 3C

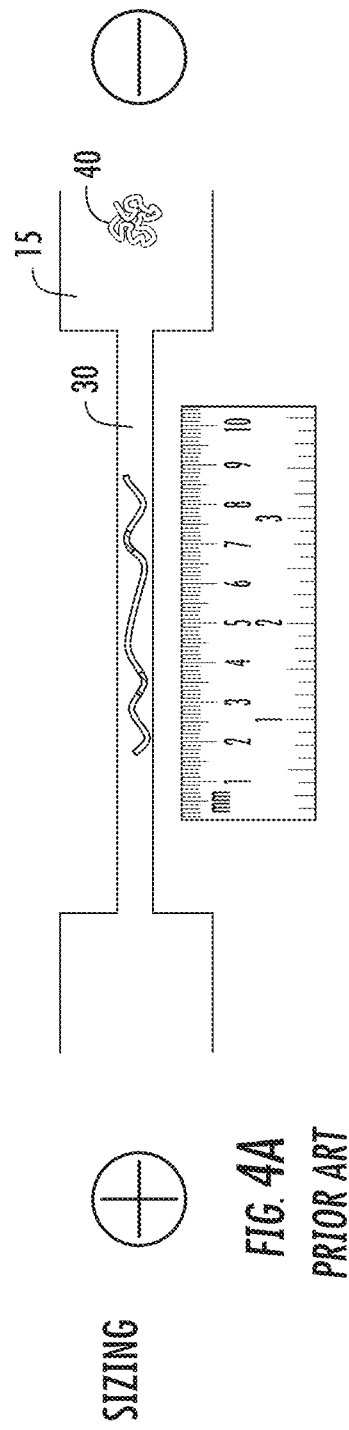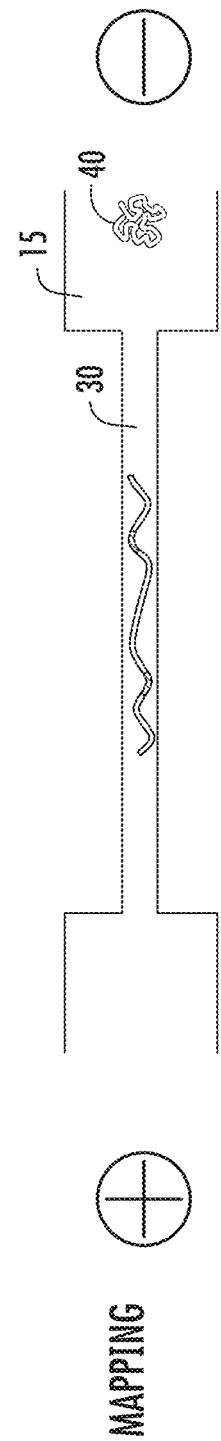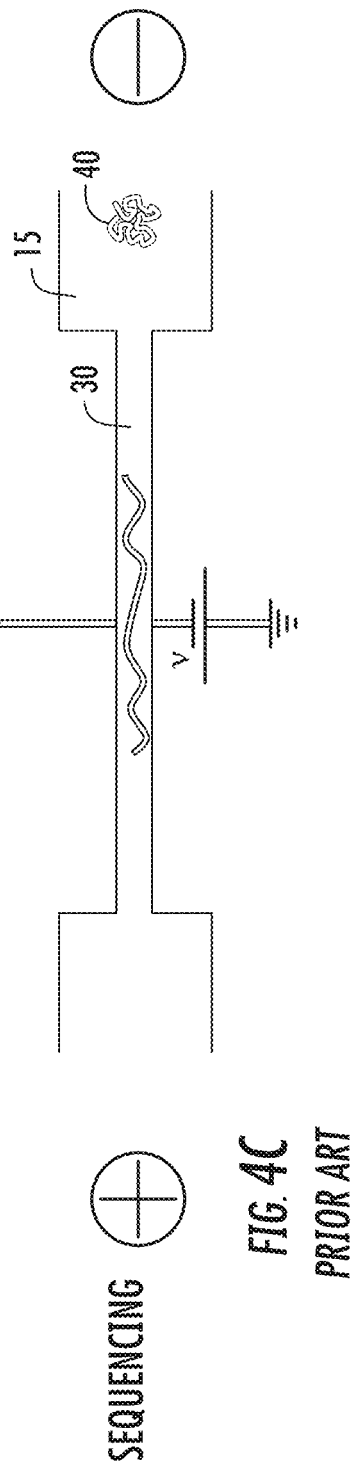

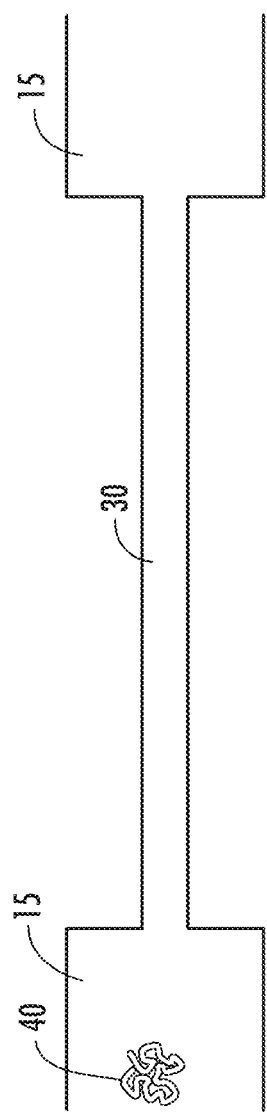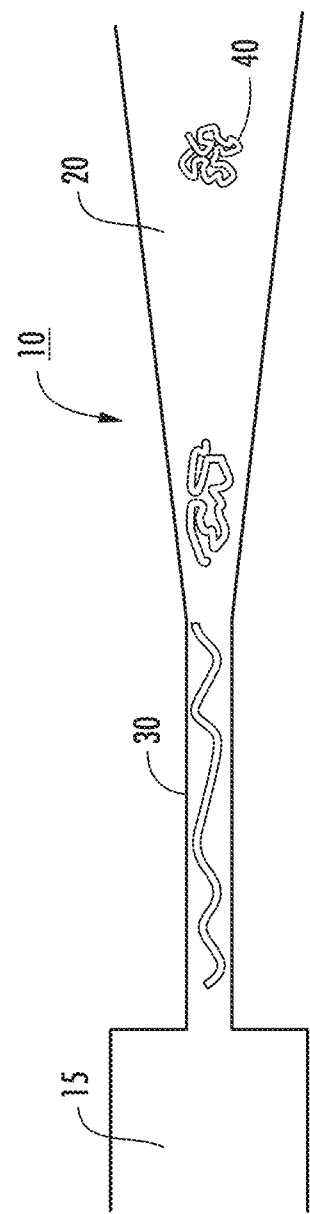

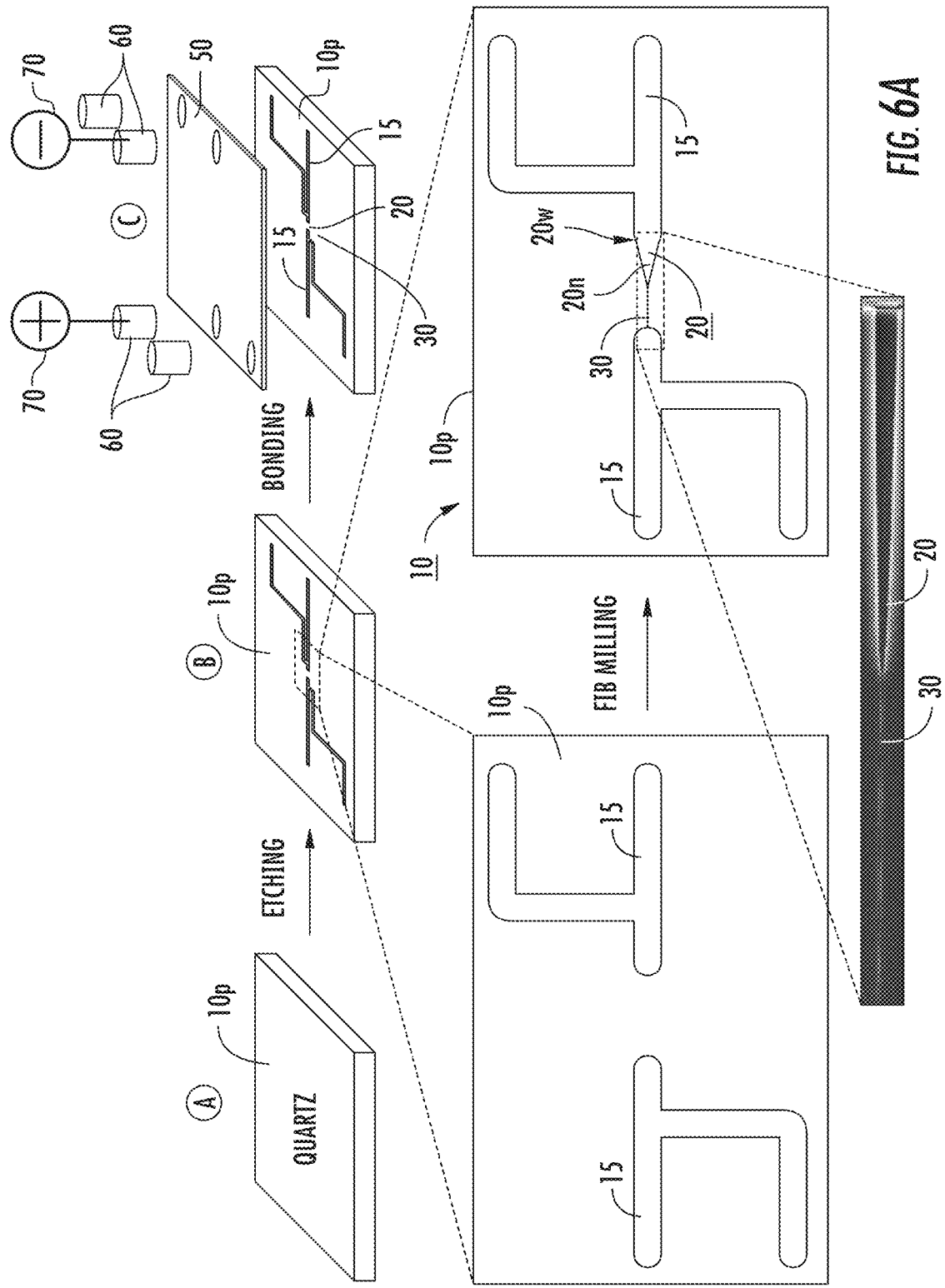

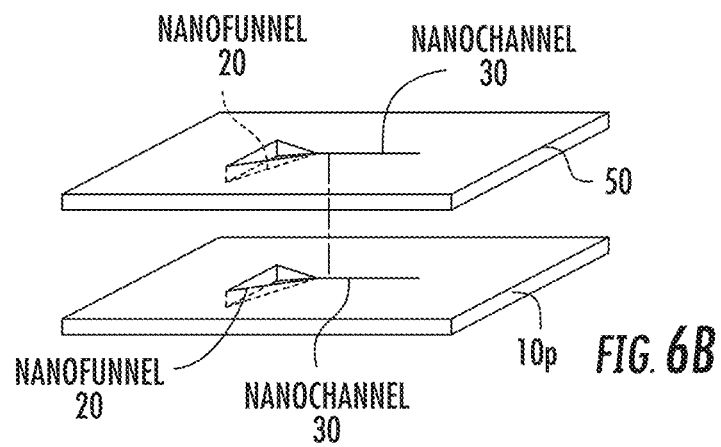
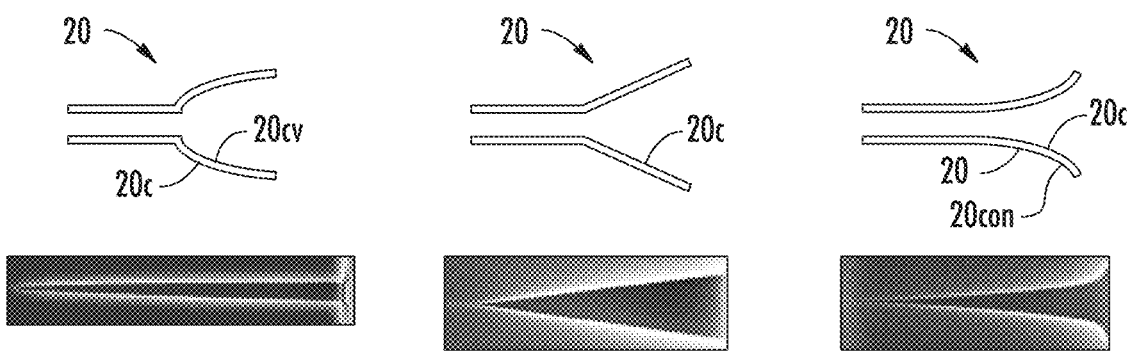
FIG. 7A    FIG. 7B    FIG. 7C

SEAMLESS CONNECTION
BETWEEN SEGMENTS

SEGMENT       SEGMENT
DEFINED BY $f_1$    DEFINED BY $f_2$

DISCONTINUOUS CONNECTION
BETWEEN SEGMENTS

SEGMENT       SEGMENT
DEFINED BY $f_1$    DEFINED BY $f_2$

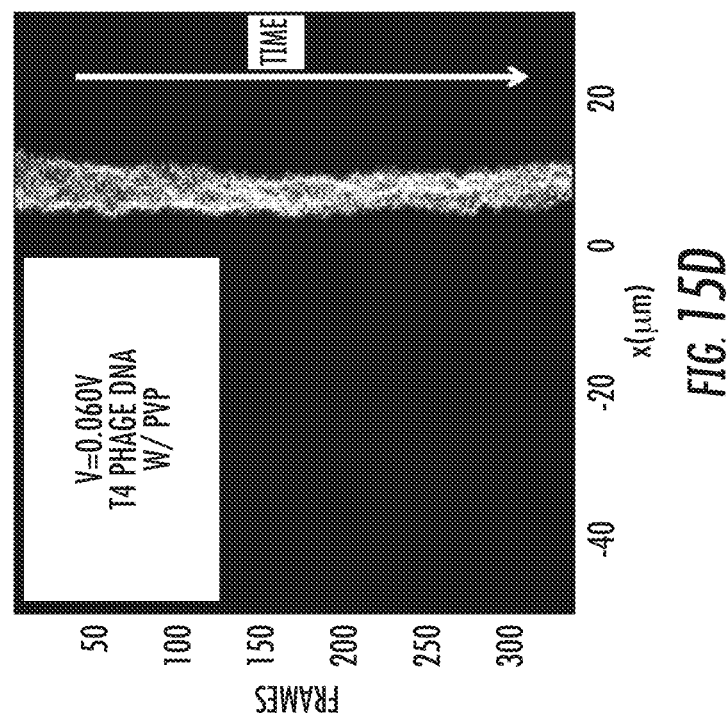
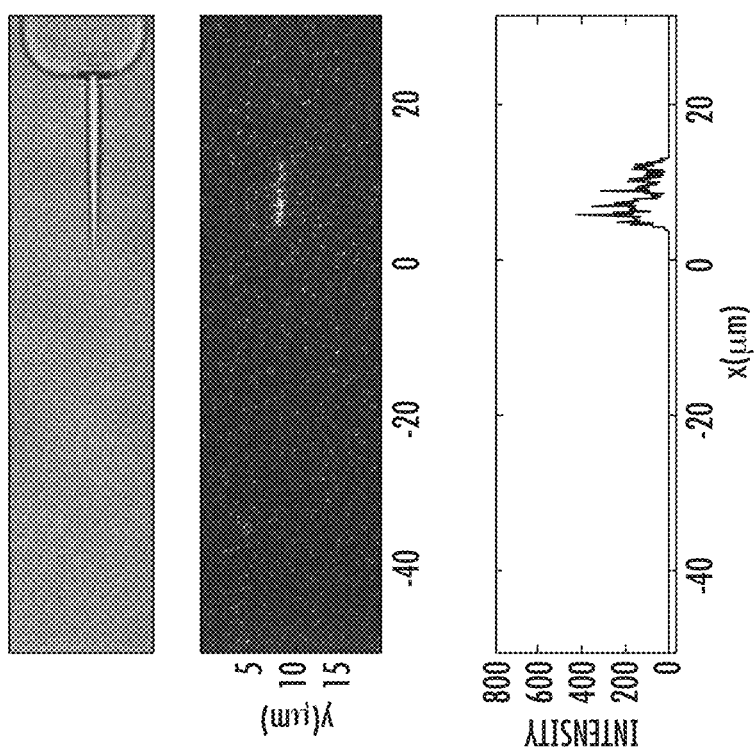
FIG. 15A
FIG. 15B
FIG. 15C
FIG. 15D

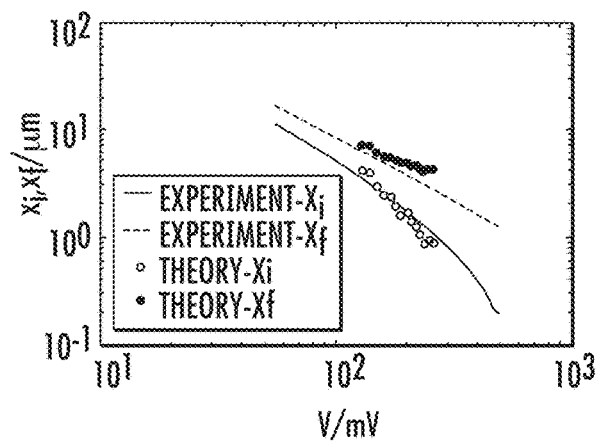 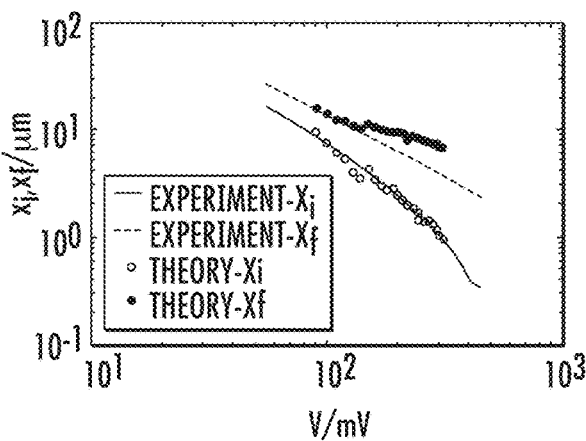
FIG. 26A  FIG. 26B
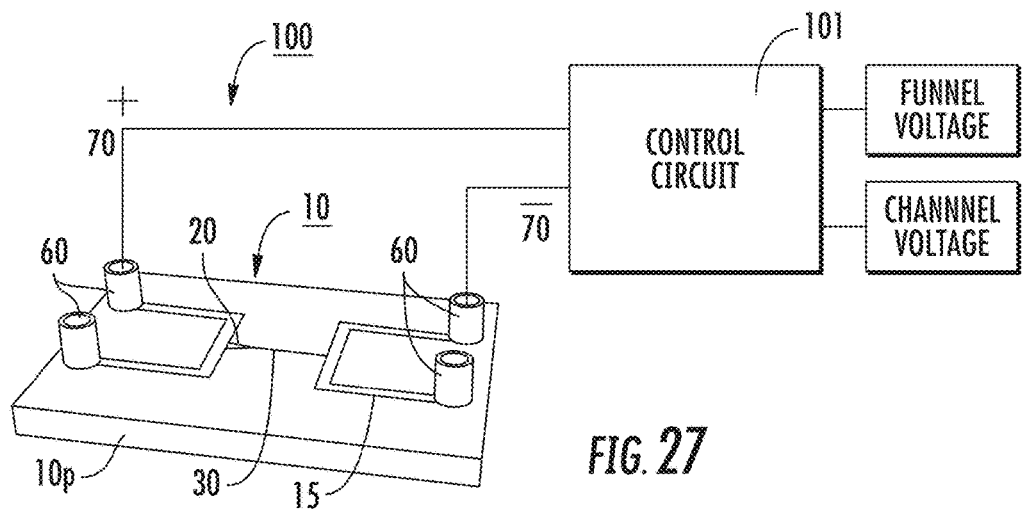
FIG. 27
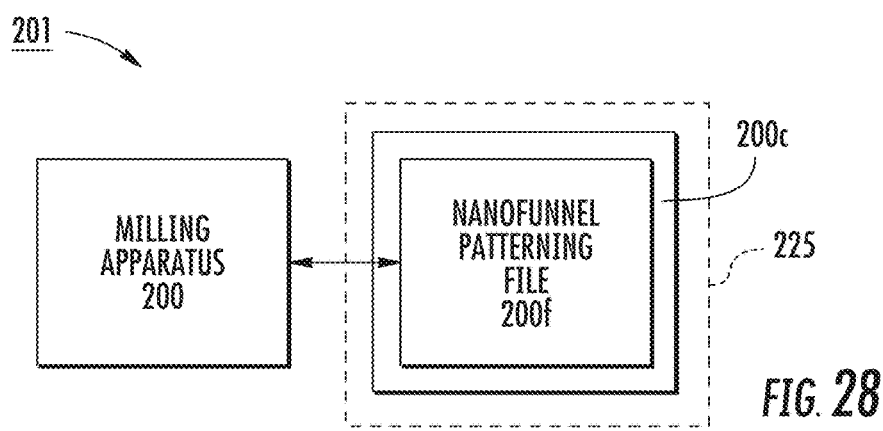
FIG. 28

DEVICES AND SYSTEMS WITH FLUIDIC NANOFUNNELS FOR PROCESSING SINGLE MOLECULES

RELATED APPLICATIONS

This application is a divisional of U.S. application Ser. No. 14/368,971, filed Jun. 26, 2014, which is a 35 USC § 371 national phase application of PCT/US2013/025078, with an international filing date of Feb. 7, 2013, which claims the benefit of and priority to U.S. Provisional Application Ser. No. 61/597,364, filed Feb. 10, 2012, the content of which is hereby incorporated by reference as if recited in its entirety herein.

STATEMENT OF FEDERAL SUPPORT

This invention was made with government support under Grant No. R01-HG002647 awarded by the National Institutes of Health. The United States government has certain rights in the invention.

FIELD OF THE INVENTION

This invention relates to fluidics and microelectronic devices.

BACKGROUND OF THE INVENTION

There has been considerable recent interest in the incorporation of nanoscale components in lab-on-a-chip fluidic devices. This interest owes its origin to several advantages (and differences that may be advantageously leveraged) in moving from the micron scale to the nanoscale. These differences can include, for example, one or more of double-layer overlap (DLO) and its effect on electro-osmosis and charge permselectivity, localized enhancement of electric fields, higher surface to volume ratios, confinement effects on large synthetic and bio-polymers, and the emerging importance of entropic effects. See, e.g., Yuan et al., *Electrophoresis* 2007, 28, 595-610; Schoch et al., *Rev. Mod Phys.* 2008, 80, 839-883; and Kovarik et al., *Anal. Chem.* 2009, 81, 7133-7140.

Nanochannels are well suited for a number of applications including single molecule detection and identification, confinement and manipulation of biopolymers, biological assays, restriction mapping of polynucleotides, DNA sizing, physical methods of genomic sequencing, and fundamental studies of the physics of confinement. See, e.g., Riehn et al., Restriction mapping in nanofluidic devices. *Proc. Natl. Acad. Sci. USA* 2005, 102, 10012; Reccius et al., Conformation, length, and speed measurements of electrodynamically stretched DNA in nanochannels. *Biophys. J* 2008, 95, 273; and Cipriany et al., Single molecule epigenetic analysis in a nanofluidic channel *Anal. Chem.* 2010, 82, 2480. It is expected that the successful implementation of at least some of the potential applications will require the careful control of molecular dynamics within the nanochannels, including the velocity of molecular transport and the frequency with which analyte molecules are driven through the nanochannels. The transport of a macromolecule from macroscopic and microscopic reservoirs through nanofluidic conduits that are smaller than the molecule's radius of gyration may require the application of a driving force (e.g., hydrodynamic, electrostatic, gravitational) to overcome an energy barrier. This barrier is primarily entropic in nature and can derive from the reduction in the molecule's conformational degrees of freedom in moving from free solution to the confining nanochannel. See, Brochard et al., Dynamics of confined polymer chains. *J. Chem. Phys.* 1977, 67, 52. Additionally, the probability of a successful transport event can be proportional to the likelihood that the molecule collides with the entrance of the nanofluidic conduit in a conformation favorable to threading. See, Kumar et al., Origin of translocation barriers for polyelectrolyte chains. *J. Chem. Phys.* 2009, 131, 194903. The practical implication of these fundamental conditions is that molecular transport does not occur until a finite threshold driving force is applied. The magnitude of the requisite force may be considerable, resulting in transport of the analyte through the nanochannel at high velocity. The energy barrier can preclude or inhibit successful transport of the analyte molecule at lower velocity through a nanochannel, such lower analyte velocities may be desirable for many applications.

SUMMARY OF EMBODIMENTS OF THE INVENTION

Embodiments of the invention are directed to devices for fluidic analysis which include at least one nanofunnel, related methods of fabricating, use of the devices and analysis systems.

Some embodiments are directed to methods of forming a chip with fluidic channels. The methods include: (a) forming at least one nanofunnel with a wide end and a narrow end into a planar substrate, the nanofunnel having a length, with width and depth dimensions that both vary over its length; and (b) forming at least one nanochannel and/or microchannel into the planar substrate at an interface adjacent the narrow end of the nanofunnel.

The forming can include milling the nanofunnel that can be carried out using and/or can include defining an electronic patterning file, e.g., a bitmap, stream file, or other computer aided design (CAD) format with desired dimensions. The milling can be carried out using focused ion beam (FIB) milling.

The forming of the at least one nanofunnel and the at least one nanochannel and/or microchannel can both be carried out during a single milling operation using an FIB milling device and a defined electronic patterning file, e.g., bitmap, stream file, or other CAD format to seamlessly connect the nanochannel to the narrow end of the nanofunnel.

The nanofunnel width and depth dimensions can be formed so that they vary in a defined geometric relationship (e.g., parabolic, convex, concave, linear, concatenated funnels) over substantially an entire length of the nanochannel to alter a cross-sectional size of the funnel from the wide end to the narrow end. This change in size may be by at least a factor of two and may vary by at least an order of magnitude.

The defined geometric shape can be a user-defined shape using an electronic patterning file, such as bitmap, stream file, or other CAD format.

The at least one nanochannel can have substantially constant width and depth and the narrow end of the nanofunnel can have width and depth dimensions that substantially match a respective width and depth dimension of an aligned corresponding nanochannel.

The nanofunnel can have a length that is (approximately) between about 1 to about 100 μm.

The method can further include sealing a flat cover to the substrate to define a nanofluidic chip adapted to analyze a molecule, such as a biopolymer that can include, for example, DNA molecules and/or proteins.

Other embodiments are directed to devices for analyzing nucleic acids or other molecules. The devices include a nanofluidic chip comprising a plurality of nanofunnels. The nanofunnels have smooth inner surfaces. Each nanofunnel has a wide end and a narrow end and varies (typically gradually) in depth and width along its length. The nanofunnels can each be connected to a respective nanochannel and/or microchannel.

The nanofunnels, where formed by FIB milling, may have at least traces of milling beam projectile material implanted in the nanofunnel inner surfaces.

The nanofunnels can have width and depth dimensions that both vary in a (e.g., user-defined) geometric relationship (e.g., parabolic, convex, concave, linear, concatenated funnels) over substantially an entire length of a respective nanochannel to alter a cross-sectional size of the funnel by at least an order of magnitude from the wide end to the narrow end.

The nanochannels can have a substantially constant width and depth, and the narrow end of the nanofunnels have width and depth dimensions that substantially match a respective width and depth dimension of a corresponding nanochannel.

The forming the nanofunnel step can be carried out by milling. The method can include, before milling the nanofunnel, providing an electronic patterning file that defines dwell times at defined X and Y coordinates to generate the nanofunnel width and depth dimensions over the nanofunnel length. The providing can be carried out to generate a nanofunnel configuration with dimensions with an associated exponent "α" defined by a power law (width, depth $\sim x^\alpha$), where x is an axial coordinate and alpha is a positive number.

The nanofunnel can have a shape with a power law exponent a configured as a function of axial position x, where $y \sim x^{\alpha(x)}$. Here "y" is understood to represent either of the dimensions width or depth. In some embodiments, the width and depth may be defined by the same function of x, yielding a nanofunnel with an aspect ratio (depth:width) of 1 along its entire length. In other embodiments, the width and depth may be defined by different functions of x, yielding a nanofunnel with an aspect ratio other than 1 (e.g., 0.1, 0.2, 0.5, 2, 4) along its entire length or an aspect ratio that varies along the nanofunnel's length.

These power laws are exemplary of a variety of geometric relationships and are not exclusive functions defining nanofunnel patterning and forming.

The nanofunnel can have a shape defined by a concatenation of functions ($y_1$, $y_2$, $y_3$, . . . ) where the width and depth of the nanofunnel are defined by $y_1$ between axial coordinates $x_0$ and $x_1$, by $y_2$ between axial coordinates $x_1$ and $x_2$, by $y_3$ between axial coordinates $x_2$ and $x_3$, and so on. Each segment of the nanofunnel can be seamlessly or discontinuously connected to its neighboring segments and the narrow end of the nanofunnel can be seamlessly connected to a corresponding aligned nanochannel or microchannel. The concatenated nanofunnels can consist of 2 to 10 segments in some embodiments or can form long fluidic conduits consisting of 10-100 or even up to hundreds or thousands of segments in other embodiments.

Still other embodiments are directed to methods of analyzing an analyte. The methods can include: (a) providing a chip with at least one nanofunnel that merges into a corresponding nanochannel; (b) applying a first voltage to cause an analyte to flow into a fluid nanofunnel; then (c) applying a second smaller voltage to cause the analyte to flow into a corresponding nanochannel; and (d) electronically or optically analyzing the molecule in the nanofunnel and/or nanochannel.

The method may also include determining molecular identification of the analyte, length of the analyte or localized functionalization mapping based on data from the analyzing step.

The applying step can be carried out so that the flow in the nanochannel is at low velocity.

Yet other embodiments are directed to fluidic analysis systems for analyzing (single) molecules. The systems include: (a) a fluidic chip comprising a plurality of nanofunnels, each funnel merging into at least one respective nanochannel; and (b) a control circuit in communication with the chip configured to (i) apply a first defined transport voltage to cause a molecule to enter at least one nanofunnel then (ii) apply a defined second transport voltage that is less than the first defined transport voltage to cause the molecule to flow into a corresponding nanochannel.

The nanofunnel width and depth dimension can vary in a parabolic relationship over substantially an entire length of the nanochannel to alter a cross-sectional size of the funnel by at least an order of magnitude from the wide end to the narrow end.

At least some of the nanochannels can have substantially constant width and depth, and the narrow end of the nanofunnels can have width and depth dimensions that substantially match a respective width and depth dimension of an aligned nanochannel.

The control circuit of the analysis system can be configured to apply the second transport voltage so that the molecule has a low velocity flow in the nanochannel.

Embodiments of the invention can be configured to allow driving transport at low velocity.

Embodiments of the invention are directed to methods of analyzing a molecule. The methods include: (a) providing a device with at least one nanofunnel; (b) flowably introducing a target molecule into the nanofunnel; (c) trapping the target molecule in the nanofunnel for a time to spatially localize the analyte molecule; and (d) analyzing the analyte molecule in the nanofunnel.

The analyte can include a single DNA molecule. Low fields ($E < E_{min}$) can momentarily trap DNA molecules but are insufficient to prevent their diffusive escape out of the nanofunnel and away from the nanochannel. Intermediate fields ($E > E_{min}$, $E < E_c$) can stably trap the DNA in the nanofunnel with the position of the DNA molecule ($x_1$ and $x_f$) dependent on the magnitude of the electric field. High fields ($E > E_c$) can transport the DNA into and through the nanochannel. Values of the field strengths $E_{min}$ and $E_c$ are dependent on the shape and size of the nanofunnel and the size of the DNA molecule.

Embodiments of the invention are directed to a Focused Ion Beam (FIB) milling system. The system includes a FIB milling apparatus in communication with or comprising at least one electronic patterning file configured to generate a nanofunnel in a target substrate.

The FIB milling apparatus is configured to generate any, some or all of the nanofunnel shapes described and/or claimed herein.

Embodiments of the invention can be carried out to evaluate DNA. The method includes obtaining a time-series of images of a single molecule of fluorescently-stained λ-phage DNA fed through a nanofunnel into a nanochannel having a depth dimension that is between about 0.5 nm to about 10 nm, typically between about 1 nm to about 5 nm (e.g., about 3 nm).

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 1 is a schematic illustration of a fluidic analysis device with a funnel-shaped entrance to a nanochannel at one end that intersects or contacts a microchannel used for sample introduction on the other end according to embodiments of the present invention.

FIG. 2 is a schematic illustration of a fluidic analysis device with a plurality of spaced apart nanochannels and respective funnel-shaped entrances according to embodiments of the present invention.

FIG. 3A is a grayscale bitmap image used to pattern a funnel according to embodiments of the present invention.

FIG. 3B is a top view SEM image of the funnel and nanochannel milled into a quartz substrate using the bitmap shown in FIG. 3A according to embodiments of the present invention.

FIG. 3C is a tilted end perspective (about 52 degrees) view of the funnel and nanochannel shown in FIG. 3B illustrating the funnel can decrease in size (width and depth as it approaches the nanochannel.

FIGS. 4A-4C are schematic illustrations of sizing, mapping and sequencing using a prior art nanochannel.

FIGS. 5A and 5B are schematic illustrations comparing DNA transport into nanochannels with (FIG. 5B) and without (FIG. 5A) the use of a funnel according to embodiments of the present invention.

FIG. 6A is a schematic illustration of a fabrication sequence that includes etching, milling and bonding to fabricate a fluidic analysis device according to embodiments of the present invention.

FIG. 6B is a schematic exploded view illustration of a device with stacked substrates according to embodiments of the present invention.

FIGS. 7A-7C are pairs of schematic illustration with corresponding (SEM) images of different exemplary geometric shaped funnel contours according to embodiments of the present invention.

FIG. 15A is a bright field optical image of an exemplary nanofunnel used for a trapping experiment for DNA according to embodiments of the present invention.

FIG. 15B is a fluorescence image of a stained DNA molecule that is stably trapped in the exemplary nanofunnel shown in shown in FIG. 15A FIG. 15C is a line profile graph of intensity versus x (μm) created from the fluorescence image in FIG. 15B and used to determine the position of the DNA molecule.

FIG. 15D is an image compiled of a series of frames similar to that shown in FIG. 15B, where for each experimental condition (e.g., voltage, DNA length, funnel shape), greater than 20 minutes of data was recorded and position and length information extracted using an analysis program according to embodiments of the present invention.

FIG. 26A is a graph illustrating a comparison between calculated (theoretical) and experimentally determined positions of the leading and tailing ends of a trapped λ-phage DNA molecule according to embodiments of the present invention.

FIG. 26B is a similar graph illustrating a comparison between calculated (theoretical) and experimentally determined positions of the leading and tailing ends of a trapped T4-phage DNA molecule according to embodiments of the present invention.

FIG. 27 is a schematic illustration of an analysis device/system using a substrate with at least one fluidic nanofunnel and associated channel according to embodiments of the present invention.

FIG. 28 is a schematic illustration of a milling apparatus in communication with and/or including an electronic patterning file for forming desired nanofunnel structures according to embodiments of the present invention.

DESCRIPTION OF EMBODIMENTS OF THE INVENTION

Figure 8B:
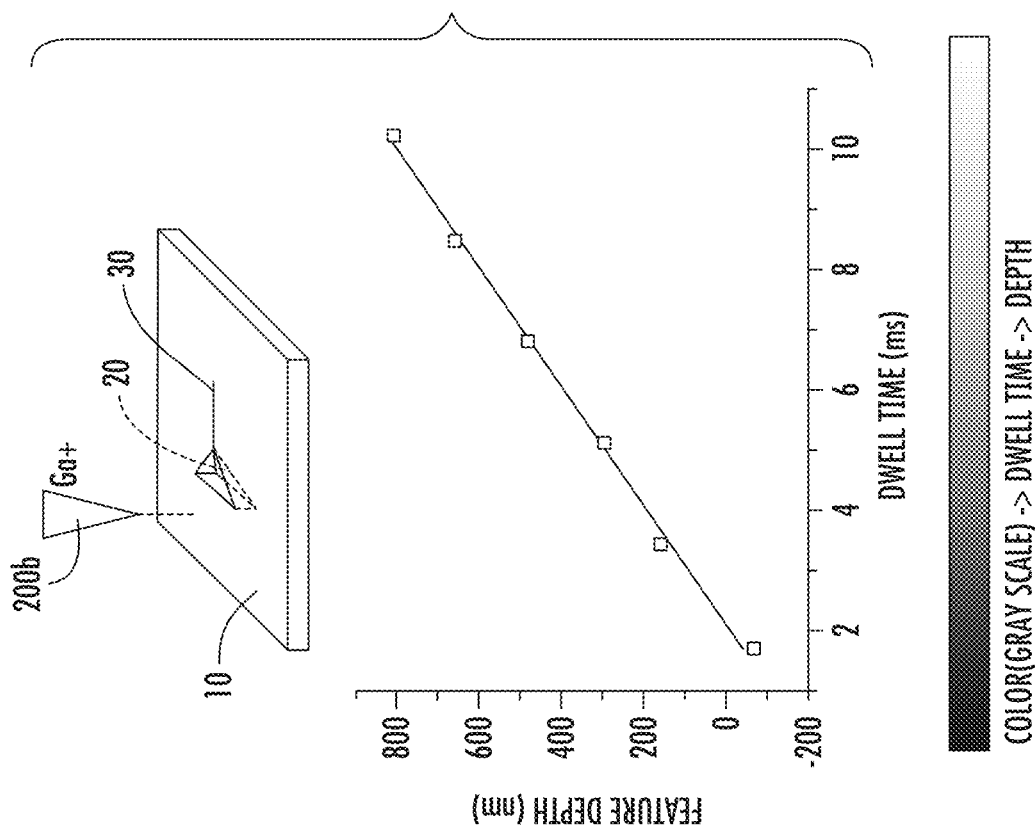
FIG. 8B is a graph of actual depth (nm) versus dwell time for ion beams into substrates that can be used to create nanofunnels according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. In some schematic illustrations, a nanofunnel may be depicted as a two-dimensional projection to clearly depict the nanofunnel shape. It should be understood that width and depth dimensions can both vary over the nanofunnel's length.

The terminology used herein is for the purpose of describing particular embodiments only and is not intended to be limiting of the invention. As used herein, the singular forms, "α", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "about" refers to a dimension or other parameter that is close to but not exactly the associated dimension or other parameter value or number, typically within about +/−20% or less, such as about +/−10% or less, than that dimension or other parameter value or number.

The term "gradually" with respect to a change in shape of a respective nanofunnel according to some particular embodiments refers to a shape that tapers inward to a smaller size.

Generally stated, embodiments of the application provide techniques using milling to fabricate nanofunnels, and optionally nanochannels, with primary (sometimes described as "critical") dimensions. The term "milling" refers to any process that forms channels using a charged particle or particles. Thus, while some examples are described herein with respect to a Focused Ion Beam (FIB) milling process, other milling processes may be used including those that employ $Ar^+$ ion beams, proton beams, $He^+$ ion beams, $Ga^+$, $In^+$, $C_{60}^+$, and electron beam milling. The term "implanted projectiles" refers to the particles implanted in the substrate nanofunnels or nanochannels in response to the milling process (based on the type of beam used to form the nanochannel). In some embodiments, devices used to analyze (fluidic) samples can comprise implanted projectiles that may be present in a trace amount (detectable with SEM or other evaluation methods), present in larger amounts or removed (e.g., via known subsequent processing techniques). The milling can be carried out to alternate charged particle milling with charged particle induced deposition processes that allows redeposition of masking material during the milling process. The redeposition of masking materials can allow for a renewal of the masking material during the etching process enabling greater aspect ratio nanochannels to be produced. The deposition of solid phase materials using focused particle beams and volatile precursor molecules is a well-established technique. (see S. J. Randolph, et al., Crit. Rev. Solid State Mat. Sci., 2006, 31, 55-89, the contents of which are hereby incorporated by reference as if recited in full herein.) A broad range of metals, insulators, and semiconductor materials can be deposited using these technique including Cr, Pt, Si and/or $SiO_2$. The redeposition process may be particularly important when milling the narrowest high-aspect ratio funnels and/or channels. These funnels and/or channels can be milled by rastering the charged particle beam across an area and/or along a line. Precursor gas of the deposited material can be injected at appropriate intervals during the beam rastering to achieve the desired nanochannel dimensions.

The term "electronic patterning file" refers to electronic (programmatic) instructions typically held in one file, but may be distributed in more than one file and on local or remote computers, to define a target nanofunnel formation pattern or image that can be used for a fabrication device such as for a milling mode of a milling instrument. The electronic patterning file can comprise one or more CAD (computer-aided design) files with milling instrument instructions/controls as to ion beam dwell time and intensity and the like. The term "bitmap" refers to computer-implemented instructions of a desired milling pattern or image for a milling mode for a milling instrument, such as an FIB milling instrument, where each pixel defines where and for how long an ion beam dwells on a target substrate. The term "stream file" refers to an ASCII text or binary file that defines the ion beam dwell time for each of a set of x, y coordinates (pixels), as listed in the file. As will be recognized by one of skill in the art, the functionality of the bitmap and stream file is the same but a bitmap is a matrix while the stream file is a list which can have subtle differences as to how the instrument patterns from the respective files.

It is noted that while the following examples describe the use of milling, and particularly, FIB milling, to form the nanofunnel, the nanofunnel and/or nanochannel (or microchannel) can be formed using any suitable apparatus or fabrication technology including for example milling, etching, molding, and embossing or combinations of the different fabrication technologies. For example, a first complementary feature can be formed, e.g., etched or milled on/in a target substrate, then the funnel construct can be formed by molding or embossing over or about the complementary feature.

The term "power law" refers to a mathematical model of nanofunnel shape and dimensions characterized by an exponential factor "alpha" where the nanochannel width (w) and depth (d) vary with position along the nanofunnel's longitudinal axis (x) by the power law $w, d \sim x^{\alpha}$. This power law may sometimes be described as $y \sim x^{\alpha}$, where it is understood that "y" represents the width and/or depth of the nanofunnel. The width and depth may be defined by the same function of x, yielding a nanofunnel with an aspect ratio (depth:

width) of 1 along its entire length. The width and depth may be defined by different functions of x, yielding a nanofunnel with an aspect ratio other than 1 (e.g., 0.1, 0.2, 0.5, 2, 4) along its entire length or an aspect ratio that varies along the nanofunnel's length. The power laws described herein are exemplary of a variety of geometric relationships and are not exclusive functions defining nanofunnel patterning and forming.

The term "nanofunnel" refers to a fluidic channel that has a three-dimensional funnel shape with two opposing ends, with one end having a wide end with a wider opening and the other opposing narrow end having a narrower opening, with the narrow end having at least one primary dimension (width and/or depth) with a nanometer size. The funnel shape may be substantially conical or frustoconical, concave or convex, but is typically formed in one or two overlying, cooperating flat substrates so that the funnel depth and width taper inward to narrow in width and also to become more shallow in depth along one direction, which may be in a flow or reverse flow direction. In some embodiments, the funnel shape can be configured to gradually decrease in cross-sectional size by at least an order of magnitude along the transit path, with the smallest dimensions being substantially equal to those of a nanochannel with which they can be seamlessly integrated (and merge into). The term "primary dimension" in the singular refers to a width and/or depth dimension with the term used in the plural to include both the width and depth dimensions. The primary dimensions of the nanofunnel at the narrow end are both typically below about 50 nm, including about 25 nm or less (on average or at a maxima), such as between about 1 nm to about 25 nm and any value therebetween, including about 5 nm, about 10 nm, about 15 nm, about 20 nm and about 25 nm. The length of the nanofunnel(s) can vary typically according to end application. These applications can include, for example, but are not limited to, a device that includes a nanofunnel that merges into a nanochannel, a device that includes a nanofunnel that connects a nanochannel with a microchannel, a device that has a nanofunnel that joins two closely spaced apart microchannels, or a device that has a nanofunnel in fluid communication with a microreservoir.

The term "nanochannels" refers to an elongate channel with sidewalls and a floor, sometimes also referred to as a "trench". The term "microchannels" refers to channels that are small but larger than nanochannels. The primary dimensions of the nanochannel(s) are both typically below about 10 nm, including about 5 nm or less (on average or at a maxima). In some embodiments, the depth and/or width can be about 3 nm or less, e.g., about 1 nm. In some embodiments, the depth is between about 1 nm to about 10 nm (on average or at a maxima) and the width is the same or larger (e.g., between about 2-10 times larger) than the depth dimension, again either measured on average or as a maxima. In other embodiments, the nanochannel can have primary dimensions up to about 100 nm. The length of the nanochannels can vary typically according to end application. However, in some embodiments the nanochannels can have a relatively short length such as about 100 nm, but are typically between about 10 microns to 100 microns. In other embodiments, the nanochannels can be longer, such as between about 0.5-12 inches (particularly when using stitching or continuous precisely controlled movements of a sample stage while milling), although are more typically between about 0.5-2 inches. The nanochannels may be linear or extend along an axis in a spiral, serpentine or other curvilinear pattern.

The nanofunnel(s) and, where used, nanochannels, can be formed into at least one solid planar substrate to have an open top surface and a closed bottom surface with the sidewalls extending therebetween. A cover may be used to seal or otherwise close the upper surface of the nanofunnel and nanochannel. The nanochannels can be configured with an aspect ratio (AR) of about 1 (e.g., the average width and average depth are substantially the same or do not vary more than about 20%) but may also have other aspect ratios, typically with the width dimension being 2-10 times greater than the depth dimension, e.g., such as an AR of about 1:3 (H (depth dimension):W). In some embodiments, the nanochannels can include aspects greater than 1, but less than 10.

The term "low velocity" refers to a velocity associated with movement of a sample, e.g., single molecule, through a nanochannel at velocities below about 0.01 cm/s. The term "low voltage driving force" refers to the voltage applied using electrodes in communication with a flow transit channel to drive transport of a sample, e.g., a molecule, into and/or through a respective nanofunnel and/or nanochannel. The low voltage driving force can be described in absolute terms or in terms of length of a fluid channel, e.g., nanochannel or nanofunnel. The low voltage driving force for a nanofunnel, where used, can be under about 5V, typically under about 1V, and for a nanochannel can be lower such as about 500 mV or less. Typically, one driving voltage is applied to drive a sample into a respective nanofunnel, typically between about 1-5V, then a smaller second voltage can be applied to move the sample into a nanochannel, the second voltage typically being below about 500 mV, such as, for example, between about 300 mV to about 200 mV.

Turning now to the figures, FIG. 1 is a schematic illustration of one embodiment of a device 10. As shown, the device 10 has a planar substrate 10p with a microchannel 15, a nanofunnel 20 and a nanochannel 30. In the embodiment shown, the nanofunnel 20 has a narrow end 20n that defines a funnel-shaped entrance into a respective aligned nanochannel 30. The wide end of the funnel 20w can reside proximate a microchannel used for fluidic sample introduction. The nanochannel 30 can have a length that is much greater than the length of the funnel 20, typically at least three times greater and more typically greater than about 5 times, 6 times, 7 times, 8 times, 9 times, 10 times or even greater length. In some embodiments, the nanofunnels 20 can have a relatively short length such as about 100 μm or less, typically between about 100 nm to about 50 μm, including about 75 μm, about 50 μm, about 25 μm, about 15 μm, about 10 μm, about 1 μm, about 500 nm, and about 100 nm or any number therebetween. In some embodiments, the length can be less than 100 nm, such as about 75 nm, about 50 nm, about 25 nm or less and any number therebetween.

Referring to FIG. 2, the device 10 can include at least one nanofunnel 20, but typically includes a plurality of spaced apart nanofunnels 20. Although shown as two spaced apart nanofunnels 20$_1$, 20$_2$, the device 10 can include more than two nanofunnels. As shown, each nanofunnel 20$_1$, 20$_2$ can merge into a respective nanochannel 30$_1$, 30$_2$ or connect other fluid structures.

The nanofunnel 20 can be configured to have dimensions in both width and depth (also described as "height") that gradually decrease by over at least an order of magnitude along the transit path. In some embodiments, the narrow end 20n with the smallest dimensions can be substantially equal to and aligned with those of a corresponding nanochannel 30 with which they can be (seamlessly) integrated.

FIG. 3A is a grayscale bitmap image used to pattern a funnel with gradually varying width and depth over its length 20*l*. FIG. 3B is a top view SEM (Scanning Electron Microscope) image of a funnel 20 and a first end of a corresponding nanochannel 30 milled into a quartz substrate using the bitmap 20*bm* shown in FIG. 3A. FIG. 3C is a top, end perspective view (tilted at 52 degrees) of the funnel and nanochannel shown in FIG. 3B illustrating the varying depth (in the length direction). In this embodiment, the funnel 20 decreases in size from about 1.5 μm×about 1.5 μm (width× depth) to about 25 nm×about 25 nm (width×depth). However, other funnel geometry and dimensions may be used.

In some embodiments, the funnels 20 can be configured to lower the threshold force needed to drive transport. This can be achieved by the gradual increase in the degree of confinement experienced by an analyte molecule as it moves along the length of the funnel 20. This effect, in combination with a force gradient that may partially be attributed to the funnel geometry, can effectively "precondition" the analyte molecule, resulting in a conformation conducive to threading into the nanochannel 30.

FIGS. 4A-C and 5A illustrate a nanochannel 30 with a fluid reservoir 60 with an analyte 40 (DNA), and without a funnel 20, which can be used for mapping, sizing and sequencing DNA. See also, Levy et al., Chem Soc Rev 39 2010, 1133; Lagerqvist et al., Nano Lett, 6 2006, 779, and U.S. Provisional Application Ser. No. 61/384,738, filed Sep. 21, 2010 (and corresponding pending PCT/US2011/052127) the contents of which are incorporated by reference as if recited in full herein. FIG. 5B illustrates the device 10 with the nanofunnel 20 that can provide an entry path for the analyte 40.

FIG. 6A illustrates a series of operations (A-C) that can be used to form devices 10 with at least one funnel 20 using milling, typically FIB milling. It is noted that the sequence of A and B may be reversed. The planar substrate 10*p* of the device 10 funnel(s) 20 can be processed to include one or more microfluidic channels 15 that can be prepared using standard photolithographic and etching techniques or other techniques (operation "A"). Next, FIB milling can be used to form an interface with a funnel 20 and nanochannel 30 in the substrate 10*p*. The funnel and nanochannel 20, 30 can be seamless and connect to the channels 15 to be in fluid communication with the channels 15 and reservoirs 60 (operation "B").

The device 10 can be a compact "chip"-like device with multiple nanofunnels 20 and nanochannels 30 and one or more associated reservoirs 60. The reservoir(s) 60 may have a short cylindrical configuration or other configuration and may be externally accessible (FIG. 6A). The term "chip" refers to a substantially flat compact body with integrated fluidic structures. The chip can be any geometric shape but is typically polygonal, such as substantially square or substantially rectangular. The chip can be in different sizes but typically has an area that is less than about 10 in$^2$ (e.g., about 25 mm×25 mm).

FIG. 6A also illustrates that electrodes 70 can be attached to the device 10, typically with positive and negative polarity at spaced apart respective reservoirs 60 to drive the transport of the fluid analyte (e.g., molecule) through the fluidic structures as is well known.

In some embodiments, the device 10 can be configured for analyzing molecules, such as nucleic acids. The device 10 can be a nanofluidic chip comprising a plurality of nanofunnels 20, each connected to a respective nanochannel 20. The nanofunnels 20 and nanochannels 30 can have a smooth inner surface (from the milling process into the substrate). The nanofunnels 20 and the nanochannels 30 can include at least traces of implanted milling projectiles from a milling beam used to form the nanofunnels 20 and the nanochannels 30, The interface between a respective nanofunnel 20 and channel 30 can be seamless in that the narrow end of the funnel 20 can have the same dimensions as the nanochannel 30. The nanochannel 30 can have a constant width and depth over at least a major portion of its length and typically over its entire length. The nanochannel 30 can be formed during a single milling operation as continuation of the milling process used to form the nanofunnel 20 or vice versa (e.g., the nanochannel can be formed first and the nanofunnel can be a continuation of that process). The term "seamless" means that there is not a seam that adjoins the two features.

The device 10 can have a planar substrate 10*p* of a variety of substrate materials, allowing device fabrication in glass, quartz, silicon, ceramics, metals, plastics, etc. In the case of electrically insulating substrate materials, FIB milling can be performed through a relatively thick (>100 nm) high quality metal film deposited on the top surface of the substrate. This metal film prevents charging during the milling process and allows milling of features with suitable tolerances and can allow critical dimensions that extend below 5 nm. See, e.g., U.S. Provisional Application Ser. No. 61/384,738, filed Sep. 21, 2010 and corresponding pending PCT/US2011/052127, and Menard, L. D.; Ramsey, J. M., The fabrication of sub-5-nm nanochannels in insulating substrates using focused ion beam milling. Nano Lett. 2011, 11, 512, the contents of which are incorporated by reference as if recited in full herein.

Figures 23A, 23B, 23C:
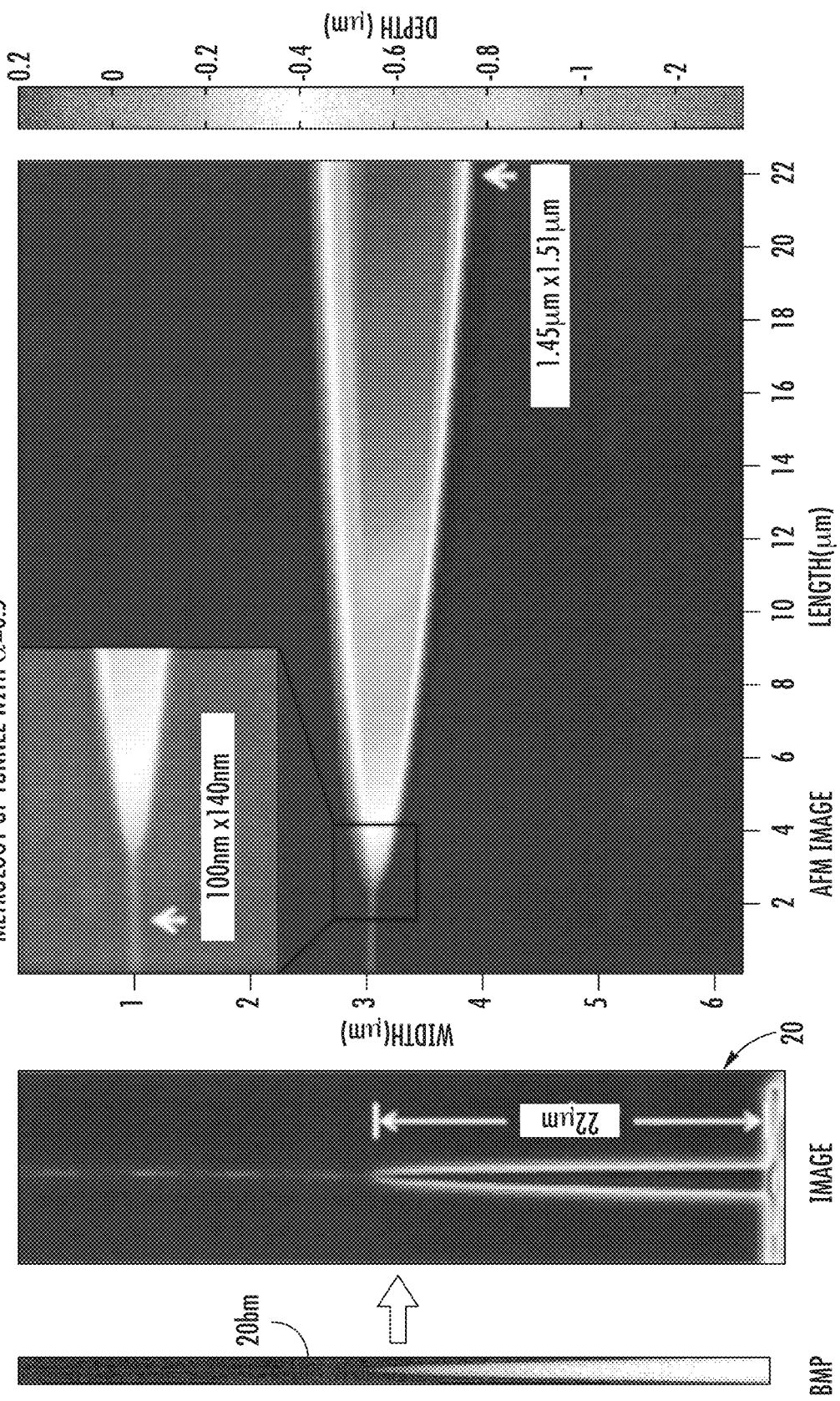
FIG. 23A is an AFM (atomic force microscopy) image of a funnel with α=0.5 according to embodiments of the present invention.
FIG. 23B is a bit map (BMP) image used to pattern the interface shown in FIG. 23A.
FIG. 23C is an SEM (scanning electron microscope) image of the interface shown in FIG. 23A.

FIGS. 7A-7C illustrates different exemplary geometric shaped funnel contours 20*c*. FIG. 7A illustrates that the nanofunnel 20 has a convex contour 20*cv*. FIG. 7B illustrates the funnel 20 has a straight line taper with walls tapering in at a (substantially) constant slope. FIG. 7C show a nanofunnel 20 with a concave contour 20*con*. FIG. 23 illustrates that the nanofunnel 20 can have a substantially parabolic relationship/shape.

Figure 8A:
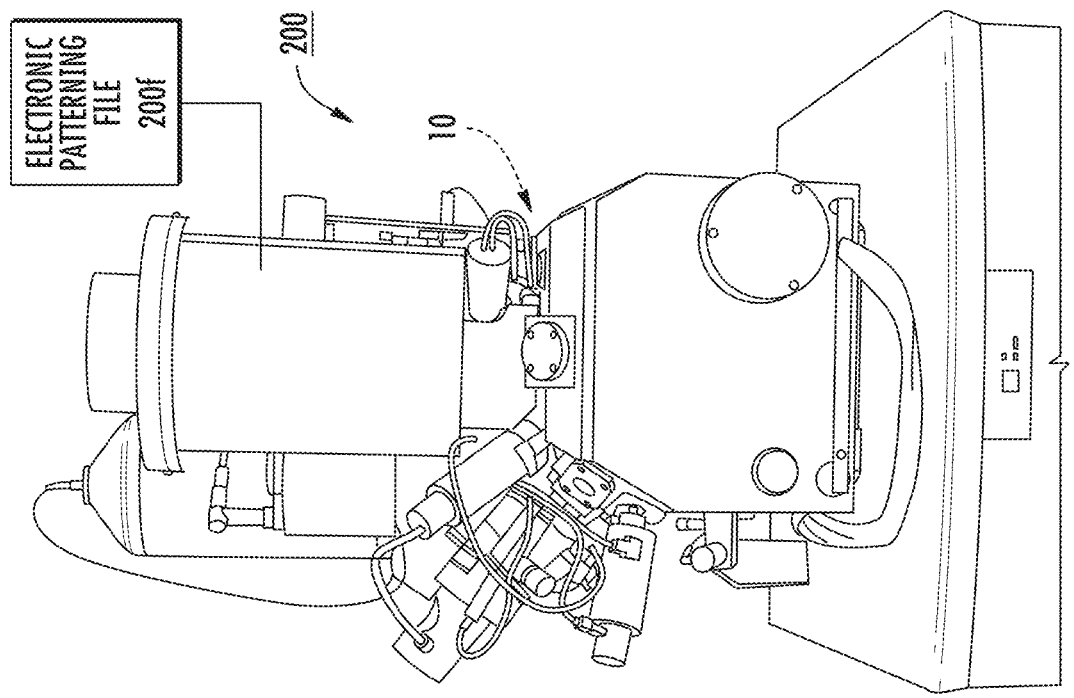
FIG. 8A is a front view of a milling apparatus with an FIB milling mode where each pixel defines where and for how long an ion beam dwells on the substrate according to embodiments of the present invention.

At "B", nanochannels 30 of a substantially constant depth can be fabricated by rastering the ion beam over a rectangular area or along a line, with each point in the rectangle or line exposed to the same ion dose. Deeper (funnel) channels can be milled by defining higher ion doses while shallower channels can be milled using lower ion doses. FIG. 8A shows an example of an FIB milling device with a BMP milling mode where each pixel can define where and how long an ion beam dwells on the substrate 10*p*. FIG. 8B illustrates an example of depth (nm) that can be set by dwell time (typically between about 1 μs to about 10 ms per pixel) with an appended gray scale graduated graph of dwell time resulting in increased depth. Because FIB milling is a direct write process, features that are relatively complex can be patterned, as described below. After FIB milling and removal of the metal film from the substrate (if used), the fluidic network comprising a funnel 20 can be sealed by bonding a cover plate 50 (operation "C") on top of the substrate using one of several possible methods such as fusion, anodic, or adhesive bonding.

In the embodiment shown in FIG. 6A, the use of two planar cooperating substrates results with the funnel formed only in the bottom substrate 10*p* results in a flat top face to the funnels 20, regardless of the geometry milled into the substrate 10*p*. FIG. 6B shows an embodiment where the funnels 20 can be configured so that both width and depth vary gradually and symmetrically around the long axis of the funnel 20. This configuration can be fabricated by milling identical funnel features and optionally a portion or all of the nanochannel 30, in both the top and bottom substrates 50, 10p, followed by bonding of the two substrates with precise alignment.

It is noted that prototypes of the device 10 were fabricated in quartz substrates because of quartz's suitability for microfluidic and nanofluidic devices. However, FIB milling of nanofluidic structures can be extended to various hard and soft materials as described in the U.S. Provisional Application Ser. No. 61/384,738, filed Sep. 21, 2010 and corresponding pending PCT/US2011/052127, which has been incorporated by reference. Examples of hard materials include, but are not limited to, substrates comprising one or combinations of: glass, quartz, silicon, and silicon nitride. The soft materials can have a low Young's Modulus value. For example, elastomers and harder plastics and/or polymers can have a range between about 0.1-3000 MPa. Examples of soft materials include, but are not limited to, polydimethylsiloxane (PDMS), polymethylmethacrylate (PMMA), and polyurethane.

As shown in FIG. 8A, a milling apparatus 200 can be configured to generate a desired shape of a nanofunnel 20 in a substrate 10. An electronic patterning file 200f (which can be provided in a number of manners including, for example, by one or more of an ASIC (Application Specific Integrated Circuit), an application ("APP"), a module and/or subdirectory file of a controller or digital signal processor) that can be held in the milling apparatus 200 or the milling apparatus 200. Alternatively, the apparatus 200 can be controlled or have access to at least one external (local or remote) device such as a processor with the electronic patterning file 200f that can generate a desired funnel shape in the substrate 10. The electronic patterning file 200f can also be distributed over various components and locations. The electronic patterning file 200f can define the dwell time per pixel of the milling beam 200b (FIG. 8B) over X, Y coordinates, or other defined coordinate systems to generate a defined nanofunnel shape. The electronic patterning file 200f can be configured as selectable different patterning instructions correlated to one or more of the following: (i) different substrate materials; (ii) different nanofunnel shapes and/or dimensions; or (iii) different target analytes.

The milling apparatus 200 can include a control circuit 200c that can communicate with at least one remote or local processor via a local area network (LAN), a wide area network (WAN) or via a global computer network, e.g., the Internet to obtain or use the electronic patterning file 200f. The milling apparatus 200 can be an FIB milling apparatus.

As shown in FIG. 28, a fabrication system 201 can comprise the apparatus 200 can include a control module or circuit 200c that can be onboard the apparatus or at least partially remote from the apparatus. If the latter, the control module or circuit 200c can reside totally or partially on a server 225 (FIG. 28). The server 225 can be provided using cloud computing which includes the provision of computational resources on demand via a computer network.

Referring to FIGS. 8A and 8B, according to some embodiments, FIB milling can be performed using a Helios NanoLab DualBeam Instrument (FEI Company) with a Ga$^+$ ion source operated at about 30 kV. This instrument is capable of using bitmap image files (20bm, FIG. 5A-7C) to define a milling pattern. The x and y coordinates of the image define where the ion beam dwells during the scan, thus achieving milling, and the gray-scale value of the pixel (0 to 255) defines the length of time that the ion beam dwells on the region of the sample corresponding to the pixel. The operator or a default configuration of the apparatus 200 and/or the electronic patterning file 200f can define the maximum dwell time, $t_{max}$. White pixels (gray-scale value equal to 255) can be exposed for a milling time of $t_{max}$ while black pixels (gray-scale value equal to 0) are not exposed to the ion beam and thus are not milled Pixels with intermediate values on the gray scale can be milled for a fraction of $t_{max}$, where the length of exposure is linearly dependent on the gray-scale value (e.g., the dwell time at a pixel with a gray-scale value of 125 is $125/255*t_{max}=0.49*t_{max}$). Color scale pixels may be used in the future.

FIGS. 3B-3C show representative scanning electron microscopy (SEM) images of a funnel with varying depth and width interfaced to a nanofluidic channel. As discussed above, FIG. 3A is an image of the original bitmap file 20bm used to mill the funnel and channel features shown in FIGS. 3B and 3C.

Measuring the Electrophoretic Mobility of DNA in 25-Nm Nanochannels

Figure 9A:
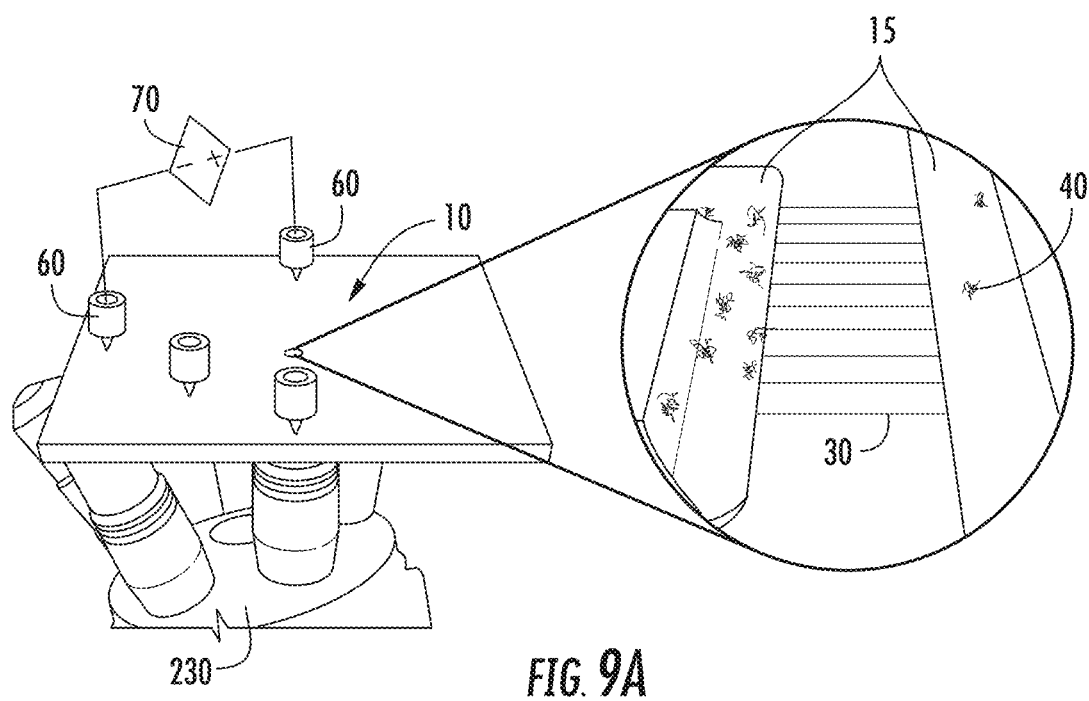
FIG. 9A is a front perspective view of a fluorescence microscope with stained DNA added to reservoirs for fluidic electrokinetic transport through the nanochannels and transport events can be observed using fluorescence microscopy (with the circle inset showing a magnified view of the nanochannel array) according to embodiments of the present invention

A series of experiments were carried out to determine the electrophoretic mobility of double-stranded DNA through 50-μm long channels having dimensions of 25 nm×25 nm (width×depth). These consisted of electrokinetically driving single λ-phage DNA molecules from one microfluidic reservoir to another through an array of nanochannels (FIG. 9A). FIG. 9A is a schematic illustration that shows an experimental setup where stained DNA solutions are added to the device reservoirs 60, DNA is electrokinetically driven via electrodes and electric field(s) through the nanochannels 30, and transport events are observed using fluorescence microscopy using a microscope 230. The inset shows a magnified view of the nanochannel array. The DNA was stained with an intercalating fluorescent dye (YOYO-1, Invitrogen) at a base pair to dye molecule ratio of 5:1. Fluorescence was excited by light from a mercury arc lamp passing through an excitation filter and a 100× oil-immersion plan apochromatic objective lens. Fluorescence from single molecules was collected through the 100× lens and imaged using an electron-multiplying CCD camera (Cascade II, Photometrics). This high sensitivity camera can collect images at frame rates up to 400 frames per second. Image analysis of individual, time-stamped frames provided information on single molecule dynamics such as molecular extension and the velocity of transport.

However, it was found that initiating translocation of the DNA molecules through nanochannels of this size required electric field strengths in the nanochannels of at least 1000 V/cm. In practice, field strengths exceeding 3000 V/cm were required to drive events with sufficient frequency to analyze a statistically significant sample of molecules. This corresponded to a velocity of ~0.9 cm/s, meaning that during translocation of the molecule through a 50-μm long nanochannel, fewer than three frames were captured. This limited data, in combination with the finite length of the λ-DNA molecules (~20 μm when stained) and the potential for image artifacts caused by the molecules' high velocity precluded the determination of electrophoretic mobility.

Figure 9B:
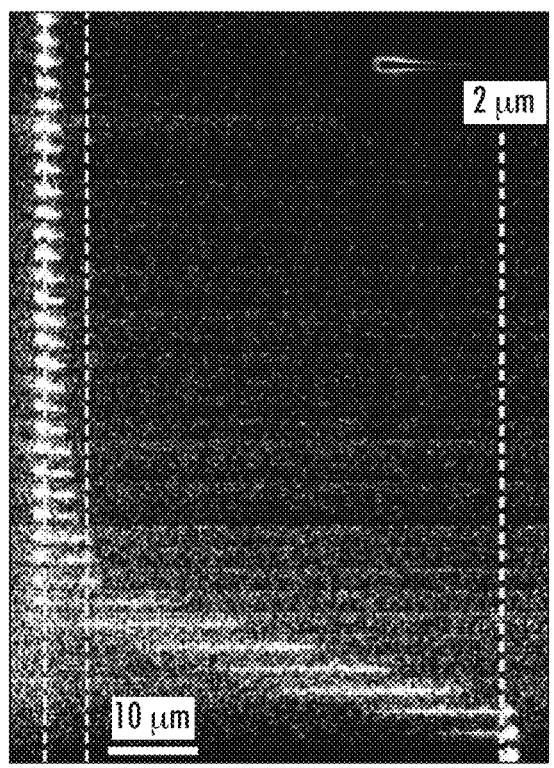
FIG. 9B is an image of a series of frames showing transport of fluorescently-stained λ-DNA molecules through a single nanochannel with a funneled entrance according to embodiments of the present invention.

In order to lower the threshold field strength to initiate the threading of single DNA molecules into the about 25 nm×25 nm channels, a device with nanochannels having identical critical dimensions but with funneled entrances was fabricated. The funnel cross-section gradually decreased in size from about 350 nm×350 nm to 25 nm×25 nm over a length of about 5 μm. The change in width and depth can be defined by a parabolic function (FIG. 7C). An SEM image of one of these nanochannel entrances is shown in the inset in FIG. 9B (top right of the figure). The threshold field strength (in the nanochannels) required to drive DNA translocation through the nanochannels in this device was about 350 V/cm, or three-fold lower than the device without funneled entrances. Consequently, it was possible to record a greater number of frames for a single translocation event and analyze these frames to determine the dynamics of transport. A representative series of frames showing transport through one of the 25-nm nanochannels with a funneled entrance is shown in FIG. 9B. Here, it is clear that the DNA molecule enters into the funnel where it slowly elongates into a configuration that then threads into the 25-nm nanochannel. In the absence of the confining funnel and at a comparable field strength, this threading process would likely progress too slowly to ensure translocation before the DNA molecule diffused away from the nanochannel entrance.

FIG. 9B illustrates a series of frames showing the transport of fluorescently-stained k-DNA molecules through a single 25-nm nanochannel with a funneled entrance. The inset SEM image shows the entrance of this nanochannel. The vertically oriented dashed lines indicate, from left to right, the entrance to the funnel, the funnel to nanochannel interface, and the other end of the nanochannel 30.

Threshold Lowering and Stable DNA Capture

The FIB milling process affords considerable flexibility in the shape and dimension of funnels 20 that can be used to interface the microfluidic and nanofluidic components on a device 10. It is contemplated that funnel geometries can be selected to minimize the applied forces, making low velocity transport possible. This may be accomplished by calculating the force applied to the DNA molecule in the nanochannel under conditions where the entropic force of the molecule's gradual confinement in the funnel is balanced by the driving force in the funnel supplied by the applied voltage, pressure, or gravitational field. Additionally, the presence of the two opposing forces may result in a range of applied voltage, pressure, or centripetal force over which a DNA molecule can be trapped in the funnel indefinitely if appropriate funnel geometries are used.

Figure 10A:
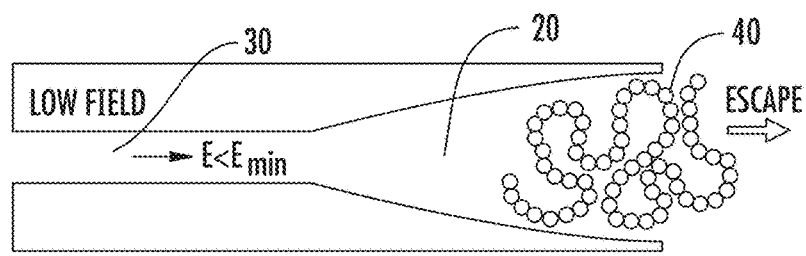
FIGS. 10A-10C are schematic illustrations of nanofunnels and DNA transport at different field strengths according to embodiments of the present invention.
Figure 10B:
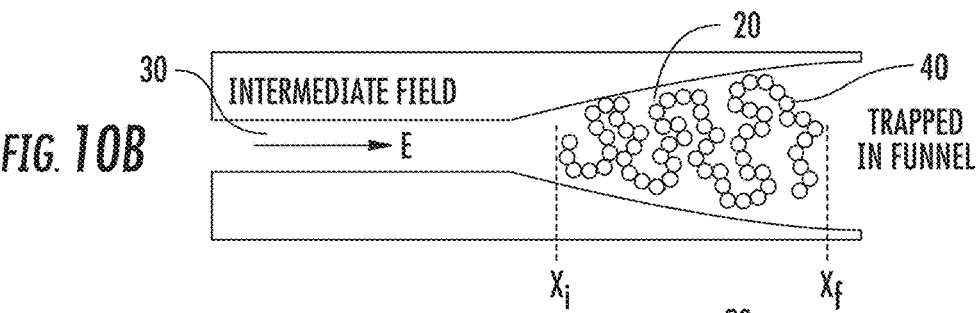
Figure 10C:
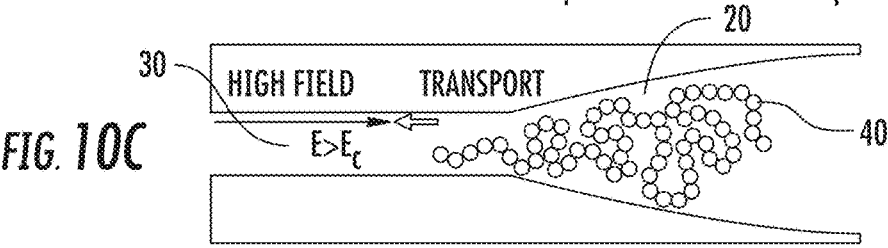

Optimal nanofunnel geometries can be determined by the theoretical modeling of DNA molecules subjected to the appropriate entropic and driving forces. In the following examples, DNA molecules are driven into and through the nanofunnels and nanochannels using an applied voltage. Similar modeling could be readily performed in which the driving force was an applied pressure or centripetal force, for example. FIGS. 10A-10C illustrate the information obtainable from these theoretical calculations. For a given funnel geometry, there is a minimum electric field strength ($E_{min}$) that must be applied to force the DNA molecule into the nanofunnel 20. Above this field strength and for some nanofunnel geometries, the DNA molecule can be stably trapped in the nanofunnel 20. As the voltage is increased, the average position of the molecule moves towards the nanochannel 30. When the electric field strength exceeds a critical value ($E_c$) the DNA molecule is forced out of the trap and is transported through the nanochannel 30. Theoretical modeling can determine the characteristic field strengths ($E_{min}$, $E_c$) that define the stable trapping regime, the average position of a trapped DNA molecule ($x_i$, $x_f$), its extended length ($x_f$-$x_i$), and the critical voltage that must be applied to drive transport through the nanochannel ($E_c$).

Low fields ($E<E_{min}$) can momentarily trap DNA molecules but are insufficient to prevent their diffusive escape out of the nanofunnel 20 and away from the nanochannel 30. Intermediate fields ($E>E_{min}$, $E<E_c$) can stably trap the DNA in the nanofunnel 20 with the position of the DNA molecule ($x_i$ and $x_f$) dependent on the magnitude of the electric field. High fields ($E>E_c$) can transport the DNA into and through the nanochannel 30. The values of the field strengths $E_{min}$ and $E_c$ are dependent on the shape and size of the nanofunnel and the size of the DNA molecule. For this reason, a theoretical understanding of DNA behavior in a nanofunnel, according to embodiments of the invention, can be important for establishing these values a priori.

Different nanofunnel shapes can be configured to be optimal for different functions. For example, one nanofunnel can dramatically reduce the voltage required to drive transport into its associated nanochannel, resulting in low velocity DNA transport. The same nanofunnel may have a very limited range of voltages over which the DNA molecule is stably trapped. In contrast, a second nanofunnel can be optimized to have a large range of voltages over which trapping in the nanofunnel is stable. This second nanofunnel may require a higher critical voltage, however, to initiate DNA transport through the nanochannel. FIGS. 11A-D illustrate some elements of nanofunnel shape that have been investigated. The nanochannel width (w) and depth (d) vary with position along the nanofunnel's longitudinal axis (x) by the power law $w,d \sim x^\alpha$.

In some particular embodiments, Equation 1 can be used to define how the nanofunnel width and depth vary as a function of position along the nanofunnel raised to exponent "α", again based on the desired nanofunnel operational characteristics. In Equation 1, the width and depth are represented by a single variable, "D" (shown in FIG. 11A), which is the effective diameter of the narrow end of the nanofunnel (equivalent to the nanochannel cross-section dimensions, y is the width or depth of the nanofunnel at position x along the longitudinal (x) axis (also known as the symmetry or longitudinal centerline axis). The variable $x_0$ indicates the coordinates of the nanofunnel apex, which is also the intersection of the narrow end of the nanofunnel with the nanochannel. Equation 1 therefore reflects that the nanofunnel is seamlessly interfaced with the nanochannel because the nanofunnel critical dimensions are equivalent to those of the nanochannel when $x=x_0$.

$$\frac{y}{D} = \left(\frac{x}{x_0}\right)^\alpha, x > x_0 \qquad \text{EQUATION 1}$$

However, it is noted that Equation 1 is provided for example only as there are other equations of similar form that could be used to stretch or compress the nanofunnel while maintaining the same alpha. Thus, any suitable power law equation can be used to select dimensions for different desired exponents (a) according to what behavior or molecule is targeted for analysis, based on the proportional relationship: $y \sim x^\alpha$. Here "y" is understood to represent either of the dimensions width or depth. In some embodiments, the width and depth may be defined by the same function of x, yielding a nanofunnel with an aspect ratio (depth:width) of 1 along its entire length. In other embodiments, the width and depth may be defined by different functions of x, yielding a nanofunnel with an aspect ratio other than 1 (e.g., 0.1, 0.2, 0.5, 2, 4) along its entire length or an aspect ratio that varies along the nanofunnel's length.

Figure 11A:
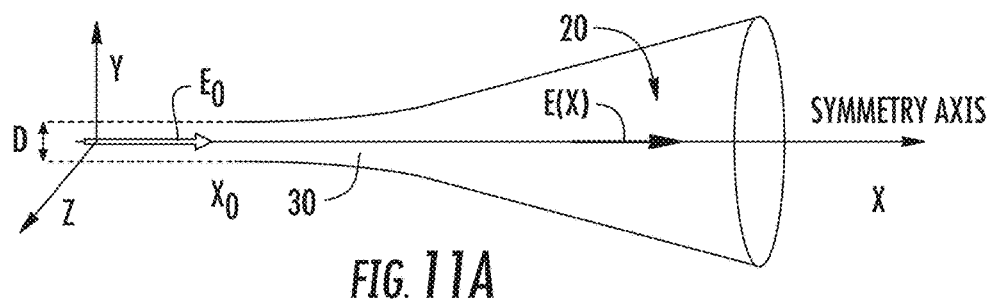
FIG. 11A is a schematic illustration of a nanofunnel with a symmetry axis and dimensional parameters for evaluating suitable electric fields for transport or trapping for various geometries according to embodiments of the present invention.
Figure 11B:
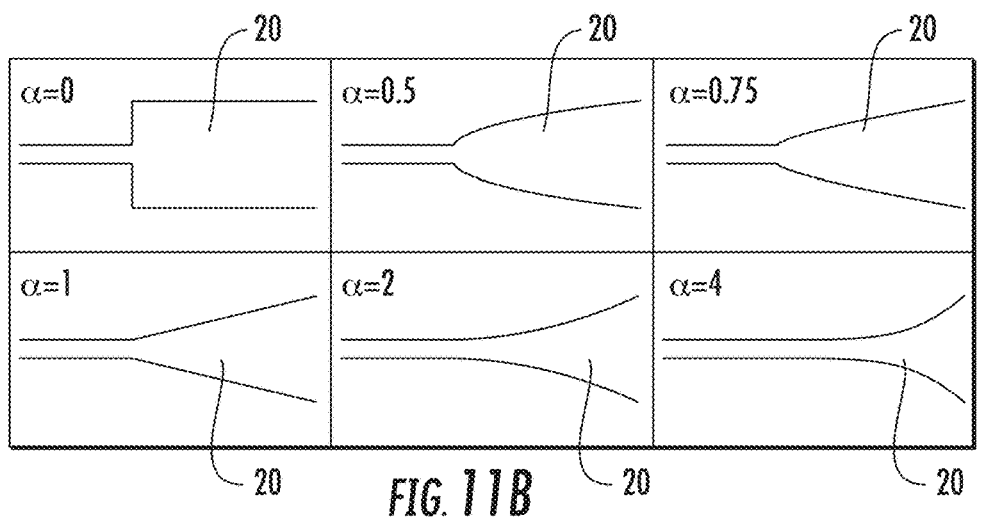
FIG. 11B is a schematic illustration of different funnel geometries with associated "α" characteristics between 0 and 4 according to embodiments of the present invention.
Figure 11C:
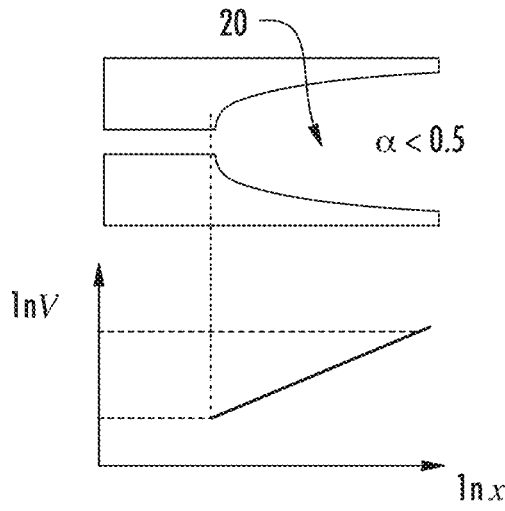
FIGS. 11C and 11D are graphs of ln V versus ln x for α<0.5 (FIG. 11C) and α>0.5 (FIG. 11D) according to embodiments of the present invention.
Figure 11D:
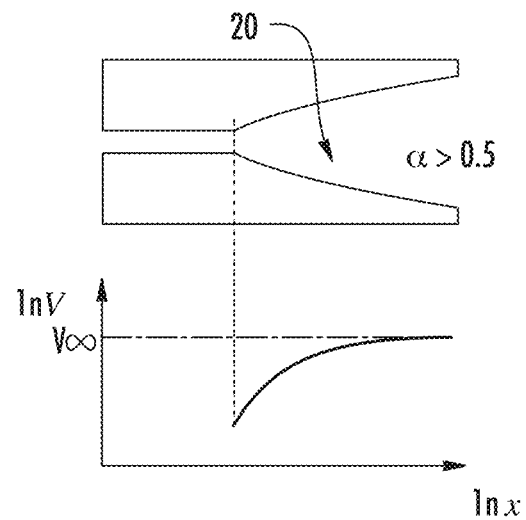
Figure 11E:
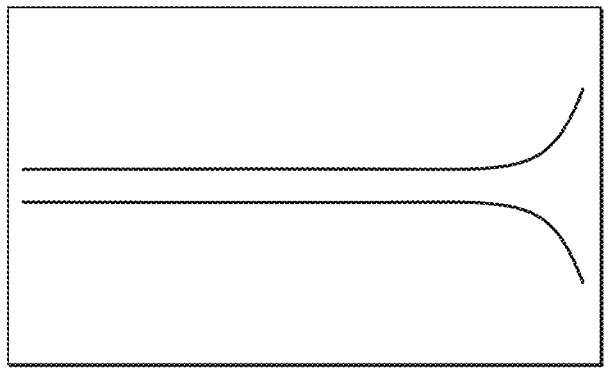
FIG. 11E is a schematic illustration of a nanofunnel that has dimensions defined by the proportionality $y \sim x^{\alpha(x)}$, where the exponent "α" is itself a function of the axial position x according to embodiments of the present invention.
Figure 11F:
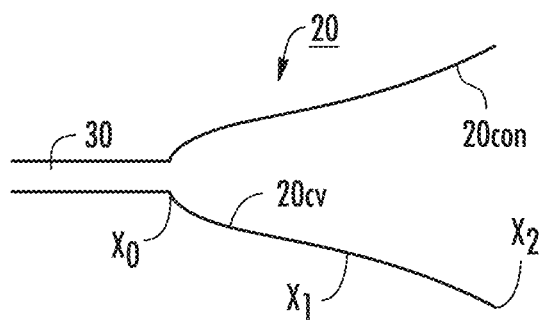
FIGS. 11F and 11G are schematic illustrations of nanofunnels that have multiple segments (also called multiple portions) where the dimensions in each segment or portion are defined by a different geometric relationship and where neighboring segments or portions are connected seamlessly (FIG. 11F) or discontinuously (FIG. 11G).
Figure 11G:
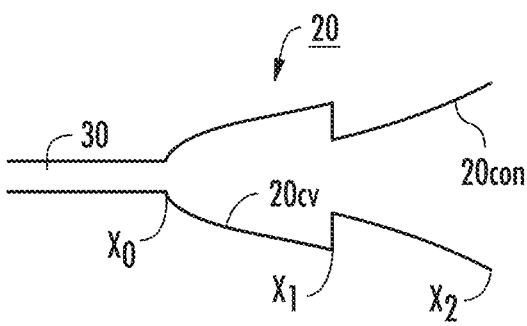

Again, as shown with FIGS. 11G and 11F, the nanofunnel 20 can have a shape defined by a concatenation of functions ($y_1$, $y_2$, $y_3$, ...) where the width and depth of the nanofunnel are defined by $y_1$ between axial coordinates $x_0$ and $x_1$, by $y_2$ between axial coordinates $x_1$ and $x_2$, by $y_3$ between axial coordinates $x_2$ and $x_3$, and so on. Each segment of the nanofunnel can be seamlessly or discontinuously connected to its neighboring segments and the narrow end of the nanofunnel can be seamlessly connected to a corresponding aligned nanochannel or microchannel. The concatenated nanofunnels can consist of 2 to 10 segments in some embodiments or can form long fluidic conduits consisting of up to hundreds or thousands of segments in other embodiments.

Figure 12A:
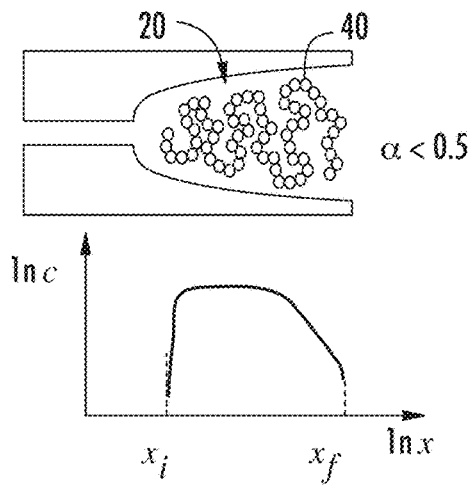
FIGS. 12A and 12B are graphs of ln c versus ln x for α<0.5 (FIG. 12A) and α>0.5 (FIG. 12B) with associated exemplary respective nanofunnels holding DNA according to embodiments of the present invention.
Figure 12B:
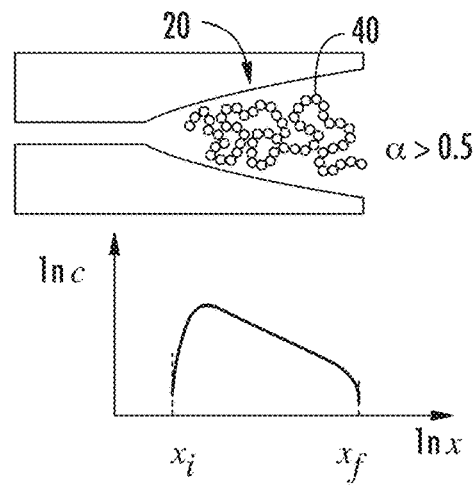

As shown in FIG. 11E, the funnel 20 can have a configuration where the exponent a can itself be a function of axial position x. This can create more complicated funnel shapes. FIG. 11E shows a simple example with an exemplary function where the exponent alpha is a function of x. By having the funnel shape defined using a proportionality, $y \sim x^{\alpha(x)}$, a variety of scaling factors and constants can be used to adjust the funnel dimensions. In this example, $y \sim x^{(0.015x+1)}$ (i.e., $\alpha(x)=0.015x+1$), but other scaling factors and exponent multipliers can be used with y dimension proportional to the x dimension. Furthermore, as shown in FIGS. 11F and 11G, nanofunnels can be configured as a series of segments where the dimensions in each segment are defined by a different geometric relationship and where the segments are connected seamlessly (FIG. 11F) or discontinuously (FIG. 11G). FIG. 11A maps an idealized cylindrical funnel onto a coordinate axis to illustrate the functional form, $y \sim x^\alpha$. Funnels for which $\alpha<1$ are convex, while those for which $\alpha>1$ are concave. FIG. 11B shows a series of funnel shapes having different a exponent values. While the power law function allows investigations over a variety of nanofunnel shapes by varying one parameter, it should not be construed as the exclusive set of funnel geometries that can be fabricated or assessed theoretically. FIGS. 11C, 11D show how the voltage, V, varies along the length of a nanofunnel when $\alpha<0.5$ (FIG. 11C) and when $\alpha>0.5$ (FIG. 11D). In these plots, a larger slope in the curve corresponds to a higher electric field at the position, x. When $\alpha<0.5$ (FIG. 11C), the voltage increases linearly along the entire nanofunnel length and can do so indefinitely. When $\alpha>0.5$ (FIG. 11D), the voltage can reach a maximum value, $v_\infty$, within the nanofunnel, above which the voltage will not increase. To be clear, there are changes in nanofunnel behavior that occur when alpha<0.5 and when alpha>0.5, including the voltage profile within the nanofunnel 20 (FIGS. 11C and 11D, bottom plots) and the monomer density profile within the nanofunnel (FIGS. 12A and 12B, bottom plots).

The nanofunnel shown in FIG. 11C has an alpha=0.3 value while that shown in FIG. 11D has an alpha=0.7 to illustrate the noted changes in behavior, not the convex or concave nature of the funnels themselves. In addition to an understanding of shape-controlled force fields, theoretical predictions of DNA behavior can consider the properties of the DNA molecule, specifically its stiffness and length. FIG. 12 shows one important way in which the properties of DNA can affect the operational parameters of trapping and critical transport voltages. Due to the voltage profile in a nanofunnel with $\alpha<0.5$, the electrostatic force on the trailing end of the DNA molecule acts like a piston, compressing the leading end of the molecule, pushing it towards the nanochannel entrance, and lowering the critical voltage needed to drive transport. This compression results in a plateau region in the plot of monomer concentration, c, as a function of position in the nanofunnel (FIG. 12A). In a nanofunnel with $\alpha>0.5$, most of the electrostatic force is on the leading end of the molecule and there is no piston effect. In this case, the monomer concentration does not exhibit a compressed plateau region (FIG. 12B).

Figure 13A:
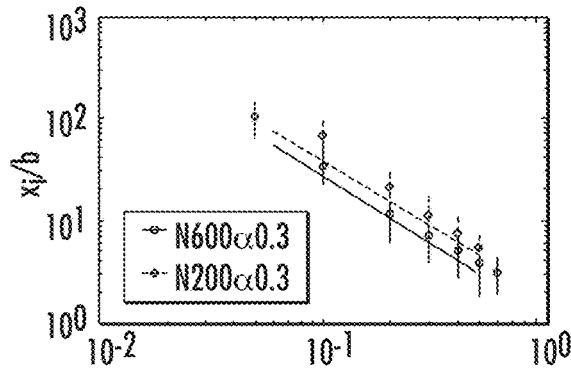
FIG. 13A is a graph of $x_i/b$ versus $qE_oD/kT$ of theory (lines) and simulation results (markers) describing the position of a DNA molecule's leading end ($x_i$) as a function of applied voltage (proportional to $E_0$, the electric field magnitude in the nanochannel) with values normalized and plotted as dimensionless variables where b is the characteristic DNA Kuhn length, q is the charge on the DNA, D is the geometric average of the nanochannel width and depth, k is Boltzmann's constant, and T is temperature for two different DNA molecule lengths according to embodiments of the present invention.
Figure 13B:
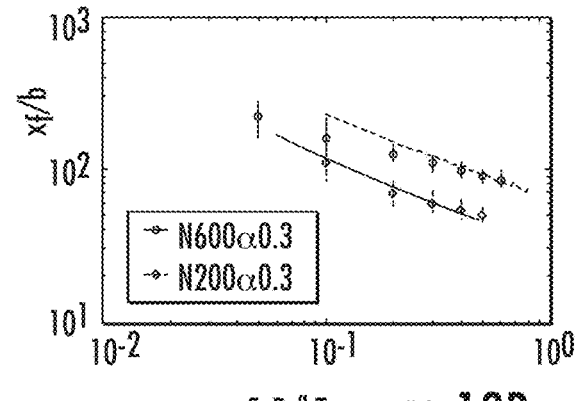
FIG. 13B is a graph similar to that shown in FIG. 13A but showing the trailing end ($x_f$) according to embodiments of the present invention.
Figure 14:
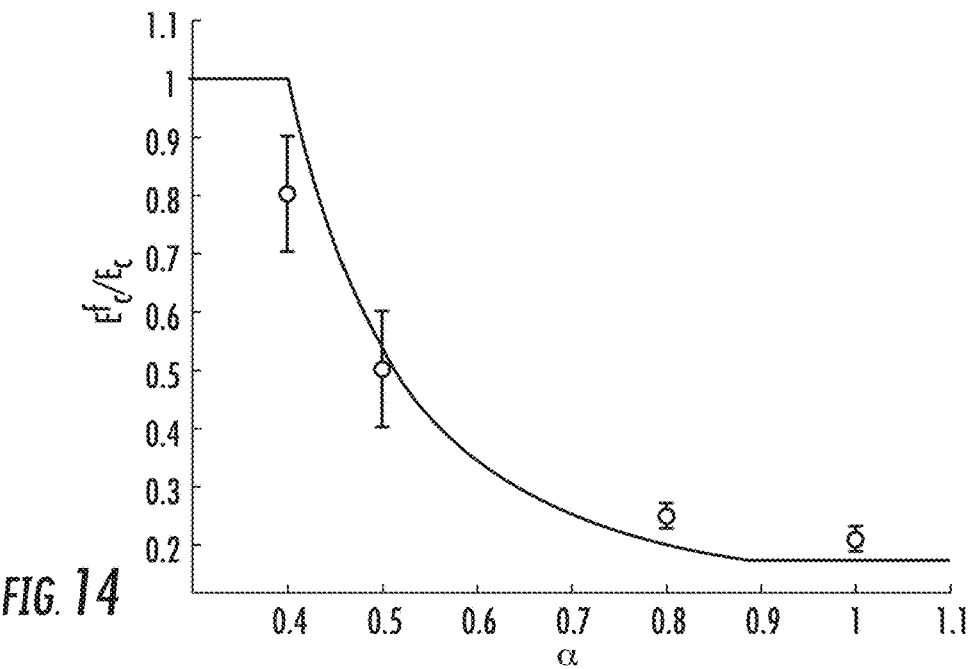
FIG. 14 is a graphical comparison of theory and simulations describing the dependence of the critical electric field required to drive transport through the nanochannel on the power law exponent, α, according to embodiments of the present invention. The dimensionless variable of the plot ordinate is the critical field with the nanofunnel $E_c^f$, normalized by the critical field necessary to drive transport through a nanochannel with no funnel, $E_c$.

The theory that was developed to describe DNA molecular behavior in nanofunnels was used to predict trends in a molecule's position, its length, and the critical electric field required to drive transport through the nanochannel. The theoretical predictions are compared to simulation and experiment results. FIG. 13A compares theory (lines) and simulation results (markers) describing the position of a DNA molecule's leading end ($x_i$) as a function of applied voltage (proportional to $E_0$, the electric field magnitude in the nanochannel). Per standard protocol in theoretical polymer physics, these values are normalized and plotted as dimensionless variables where b is the characteristic DNA Kuhn length, q is the charge on the DNA, D is the geometric average of the nanochannel width and depth, k is Boltzmann's constant, and T is temperature. Results are plotted for DNA molecules that are 200 (diamonds) and 600 (circles) Kuhn lengths long, or approximately 20 and 60 µm, respectively. FIG. 13B shows the position of the DNA molecule's trailing end ($x_f$) as a function of applied voltage. The equilibrium length of the DNA molecule can be determined by the difference, $x_f - x_i$. FIG. 14 shows a comparison of theory and simulations describing the dependence of the critical electric field required to drive transport through the nanochannel on the power law exponent, $\alpha$. The dimensionless variable of the plot ordinate is the critical field with the nanofunnel $E_c^f$, normalized by the critical field necessary to drive transport through a nanochannel with no funnel, $E_c$.

Experimental investigations were conducted to determine the behavior of DNA molecules in a nanofunnel. Similar to the theoretical efforts, the parameters that were measured included the voltage range of stable trapping, the position of a trapped DNA molecule, its equilibrium length, and the critical electric field at which transport through the nanochannel occurs. Fluorescently stained λ-phage and T4-phage DNA molecules were electrokinetically driven into a funnel at field strengths greater than $E_{min}$. The position of the molecule within the nanofunnel was monitored, typically for over 30 min, and plotted as a function of time. This data acquisition protocol was repeated over a range of voltages within the stable trapping regime to determine the dependence of the molecule's position and length on the applied voltage.

Figure 16:
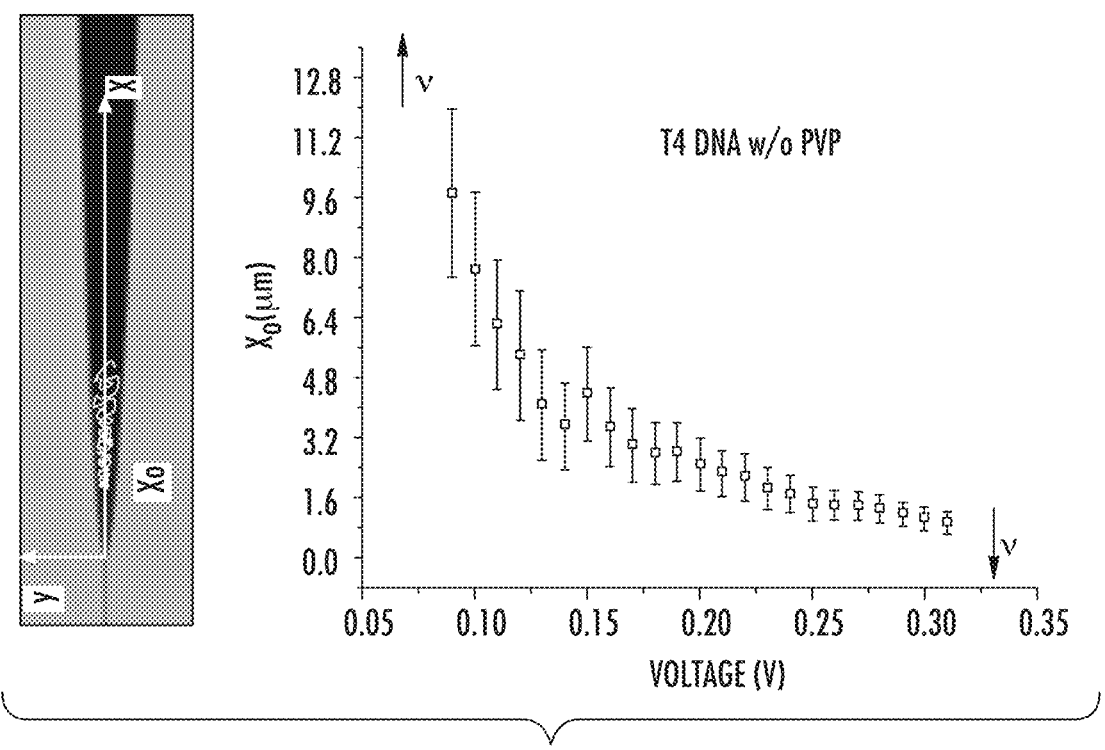
FIG. 16 is a graph of experimentally determined position $x_o$ versus voltage (V) for DNA as shown by the appended image of the DNA in the nanofunnel according to embodiments of the present invention.
Figure 17:
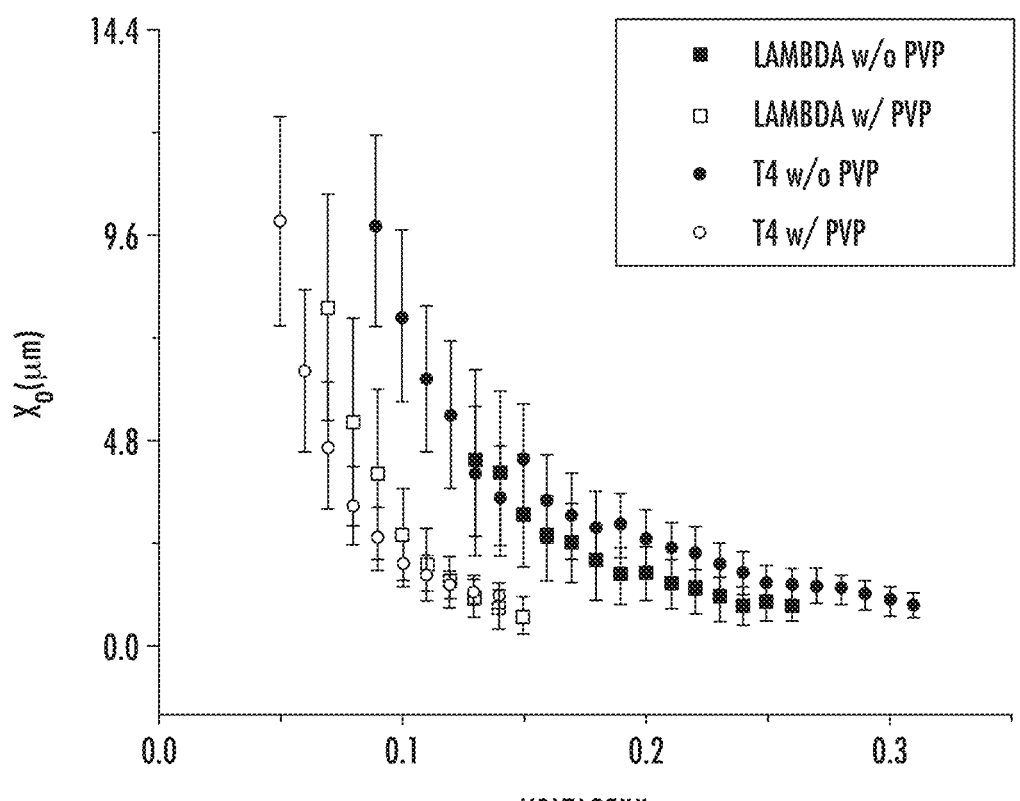
FIG. 17 is a graph of experimentally determined position $x_o$ versus voltage (V) for DNA for lambda (λ) and T4 DNA with and without PVP (polyvinylpyrrolidone) according to embodiments of the present invention.
Figure 18:
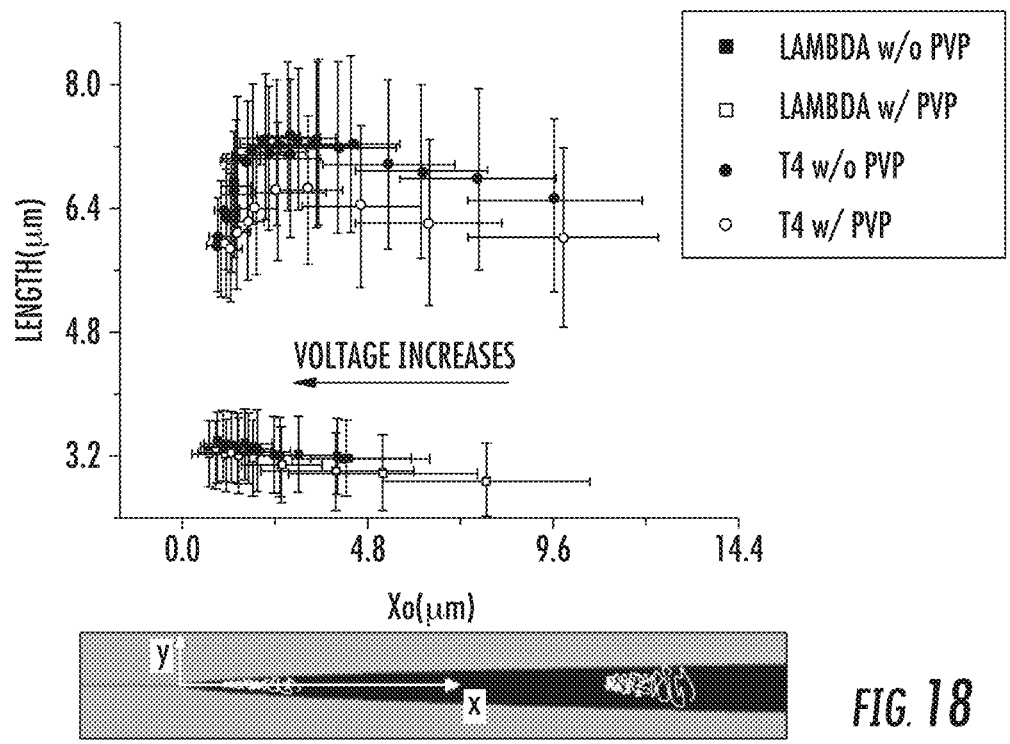
FIG. 18 is a graph of experimentally determined length changes (length versus $x_o$) at various voltages for lambda and T4 DNA with and without PVP according to embodiments of the present invention.

FIG. 15 are graphs and images from a trapping experiment. DNA molecules were trapped in the nanofunnels shown in FIG. 15A. Fluorescence images were recorded (FIG. 15B) and reduced to an intensity profile (FIG. 15C) characterizing DNA length and position. FIG. 15D shows a time series of these frames highlighting the thermal fluctuations in the molecule's length and position. FIGS. 16 and 17 are graphs of the voltage dependence of trapping position for two DNA molecules having different contour lengths (λ-phage, ~20 µm long, and T4-phage DNA, ~70 µm long) in an electrophoresis buffer and in some instances, as indicated, containing 2% by weight of a low molecular weight polymer, polyvinylpyrrolidone (PVP). FIG. 18 is a related graph that illustrates the relationship between the voltage-dependent properties of DNA length and trapping position. These two values are correlated because the greater confinement experienced by the DNA molecule as it is driven deeper into the funnel results in greater extension. The variances in these parameters provide a measure of the trap stability vis-à-vis thermal fluctuations. Each data point in FIGS. 16-18 represents the average of over 20,000 measurements collected over about 30 minutes.

It is contemplated that the use of properly shaped and sized funnels 20 can facilitate macromolecule capture, trapping, and transport through nanochannels 30 having critical dimensions smaller than the radius of gyration of the molecule. By lowering the threshold force needed to drive translocation, greater control over molecular transport dynamics may be achieved. For channels 30 with nanoscale dimensions in width and depth, confinement of the macromolecule in both of these dimensions is disfavored by an entropic energy barrier. Therefore, the optimal funnel geometry can provide a gradual increase in confinement in both dimensions. This can be achieved by patterning funnels using FIB milling in which the lateral dimensions and shape of the funnel are controlled by the pattern over which the beam is rastered. The depth of the funnel is controlled by varying the dwell time of the ion beam, milling deeper features at the funnel mouth and gradually shallower features towards the intersection of the funnel and nanochannel. The introduction of such funnels at the entrance to nanochannels has been predicted theoretically and verified experimentally to reduce the voltage that must be applied to electrokinetically drive double-stranded DNA through long FIB-milled nanochannels. Additionally, given appropriate funnel geometries and capture forces, single molecules can be stably trapped and investigated for a desired length of time.

The devices 10 and/or nanofunnels 20 can be configured to analyze a DNA molecule, a protein, a fluorescently stained molecule, and optionally the analyte molecule can be been modified in any way to provide or enhance analyzing the molecule in a respective nanochannel 20.

The use of FIB milling to fabricate features with control in all three dimensions provides an ultimate degree of flexibility in funnel design. A macromolecule can be gradually driven through an FIB-milled funnel directly into a nanochannel, transitioning from an unconfined to a highly confined state. This gradual transition can result in translocations occurring at low molecular velocities in which the molecule preferentially enters the nanochannel in an unfolded, extended state.

The use of funnels to facilitate the threading of macromolecules into nanochannels lowers the threshold force needed to drive translocation and thus lowers the transport velocity, which is expected to enable more precise optical and electrical measurements on single confined molecules. One example is the sequencing of DNA molecules in a nanochannel interfaced to opposed tunneling probes in which base calling is achieved by measuring the unique tunneling currents through the individual nucleotides. Such a funnel could also be used in isolation (without interfacing it to a long nanochannel) as a conduit between two microchannels and serving as a stochastic sensor. Translocations through the funnel could be monitored optically (e.g. fluorescently stained molecules) and/or electrically (e.g., axial ionic current). A potential advantage to this geometry is the seamless integration of microfluidic and nanofluidic components on a single layer device, in contrast to stacked devices that integrate microfluidic channels and nanoporous membranes. Funnels 20 in which both the width and depth vary gradually are also believed to be suitable, potentially ideal, platforms upon which to study the physical properties of flexible or deformable macromolecules. Because the FIB milled nanochannels and nanofunnels are easily interfaced with other fluidic components on a single chip their use can be integrated with other technologies such as flow injection, separations in microfluidic channels, and single cell lysis.

The described nanofabrication methodology and devices have application to microelectronics and nanofluidics technology. Nanofluidic implementations with nanochannels of these critical dimensions and quality are well suited for a number of applications including single molecule detection and identification, confinement and manipulation of biopolymers, biological assays, restriction mapping of polynucleotides, DNA sizing, physical methods of genomic sequencing, and fundamental studies of the physics of confinement.

Figure 19:
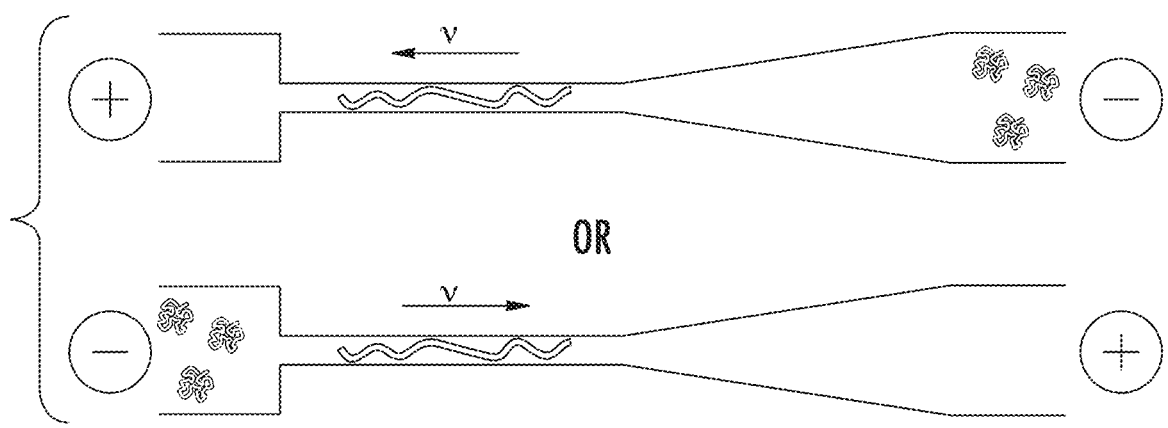
FIG. 19 are schematic illustrations of a nanofunnel that merges into the nanochannel with DNA and two alternate drive directions and event frequency according to embodiments of the present invention.
Figure 20:
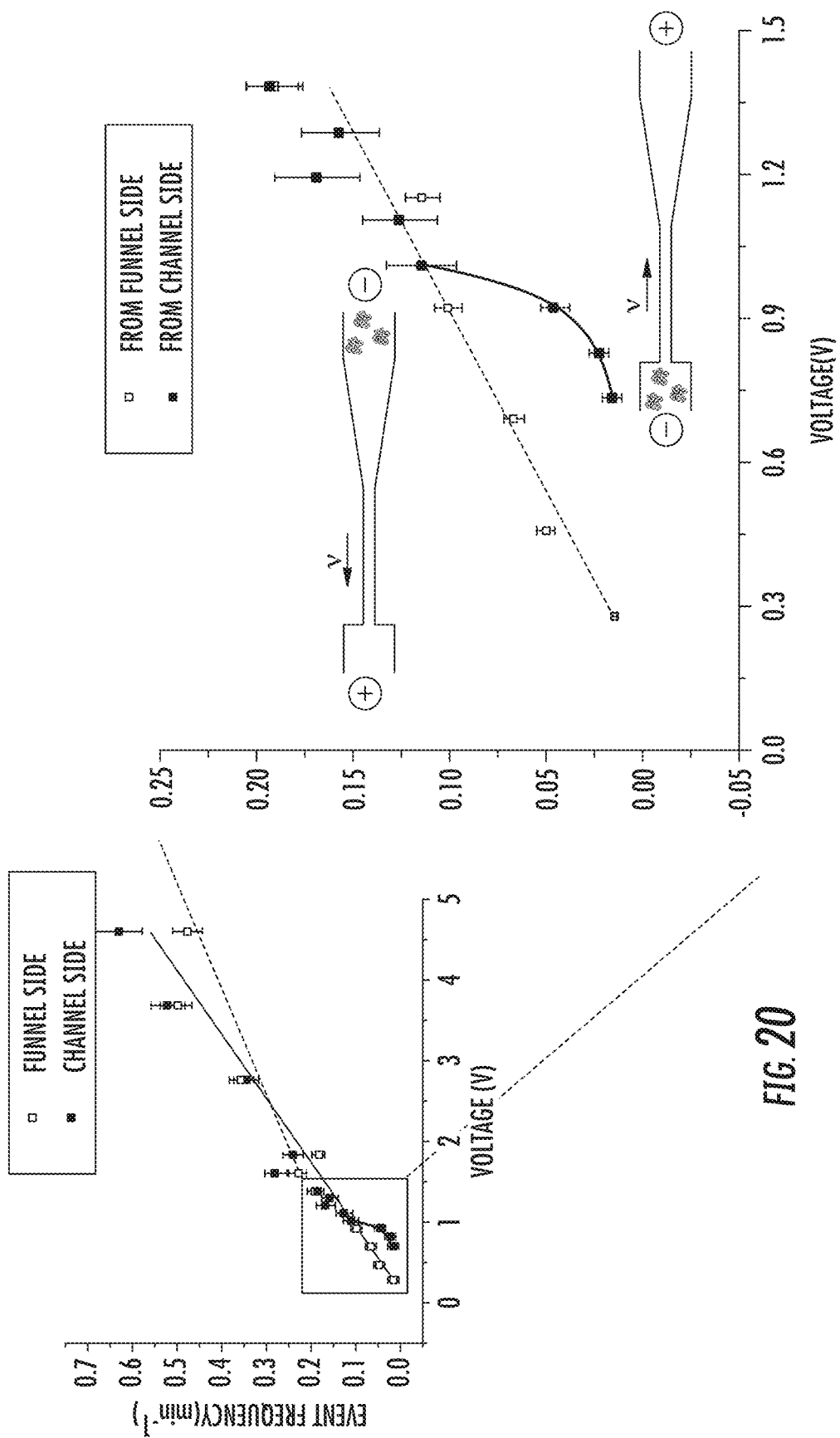
FIG. 20 is a graph of experimentally determined event frequency ($min^{-1}$) versus voltage (V) with a portion exploded for ease of reference with an appended schematic of the drive direction (funnel side and channel side) according to embodiments of the present invention.
Figure 21:
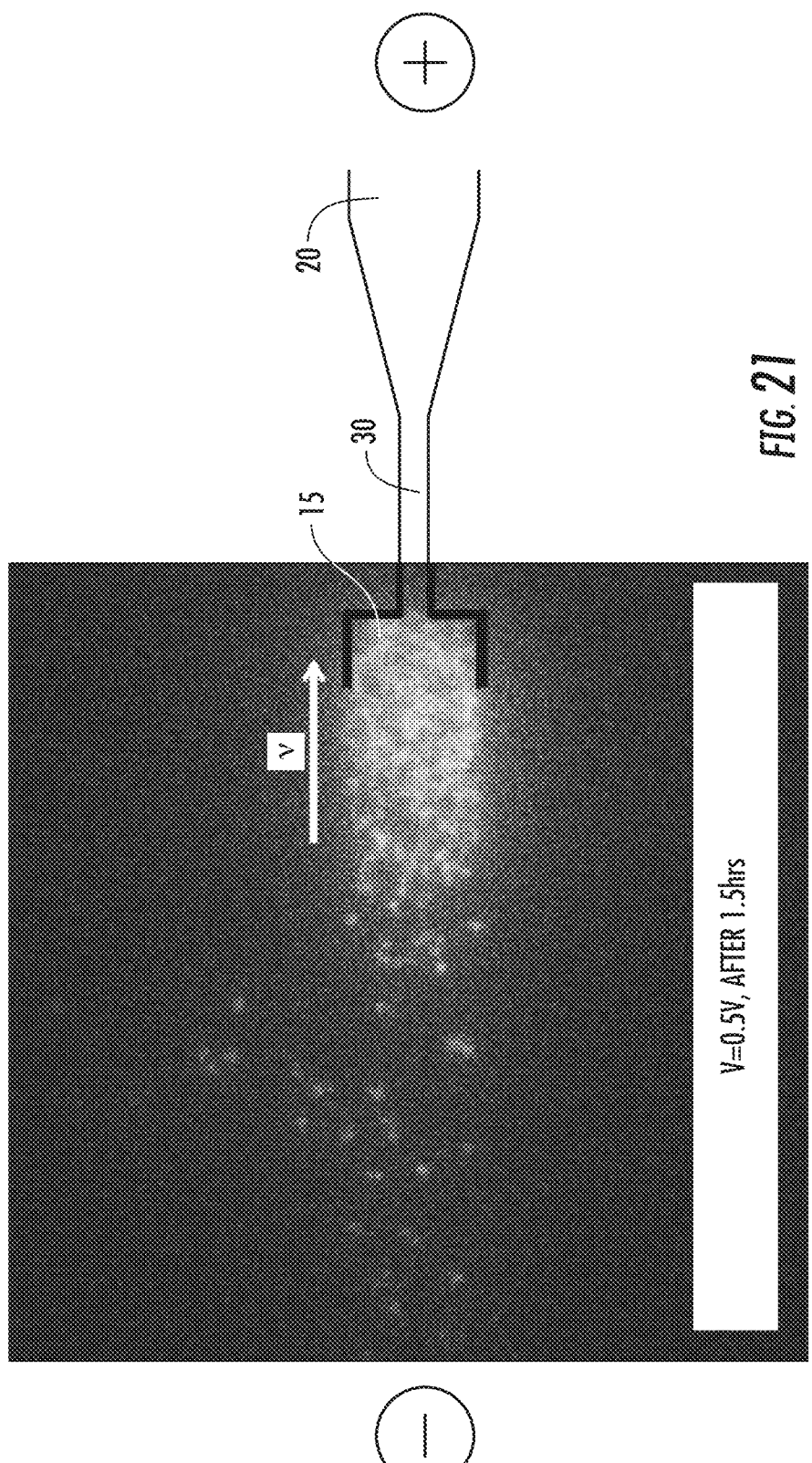
FIG. 21 is an image of a nanochannel illustrating DNA and its concentration at the nanochannel entrance when a voltage less than the energy barrier is applied for a period of time (V=0.5V after about 1.5 hours) according to embodiments of the present invention.

FIG. 19 is a schematic illustration showing experimental evaluations of translocation event frequency for DNA molecules electrokinetically driven through the nanochannel from either the funnel side (right to left in FIG. 19) or the channel side (left to right in FIG. 19). FIG. 20 shows the experimental results of the two experiments shown in FIG. 19. The linear increase of translocation event frequency with applied voltage at higher voltages indicates that voltages in this range exceed the entropic barrier value. In the case of translocations originating from the channel side, the exponential region of the data seen at low voltages indicates the presence of an entropic barrier. This barrier is not observed in translocations originating from the funnel side. FIG. 21 is a fluorescence microscopy image that shows further evidence for the existence of an energy barrier to translocation from the channel side. By applying a voltage (0.5 V) below the threshold for an extended period (1.5 hours), DNA molecules were electrophoretically driven to the nanochannel entrance but the force on the molecules was insufficient to drive translocation. This condition results in DNA concentration at the nanochannel side. The critical electric fields, $E_c$, to drive DNA transport into and through the nanochannels for different nanofunnel geometries and DNA samples are presented in the table below. All of the nanofunnels have the same length and have a width×depth that increases from about 100 nm×about 100 nm at the nanochannel end (equivalent to the nanochannel width×depth) to about 1.5 μm×about 1.5 μm at the nanofunnel entrance that is interfaced to the microchannel. The nanofunnels differ in the exponent, α, that defines their shape.

TABLE 1

ELECTRIC FIELD REQUIRED TO DRIVE DNA INTO NANOCHANNEL

| NANOFUNNEL SHAPE | CRITICAL ELECTRIC FIELD FOR EACH DNA SAMPLE (V/cm) | | |
| --- | --- | --- | --- |
| | λ-PHAGE (~20 μm length) | T4-PHAGE (~70 μm length) | CIRCULAR CHAROMID DNA (~18 μm circumference) |
| α = 0 | 65 ± 7 | 65 ± 7 | 65 ± 7 |
| α = 0.5 | 16.1 ± 0.7 | 17.5 ± 0.7 | 21.7 ± 0.7 |
| α = 1 | 10.8 ± 0.7 | 10.8 ± 0.7 | 12.3 ± 0.7 |

Figure 22A:
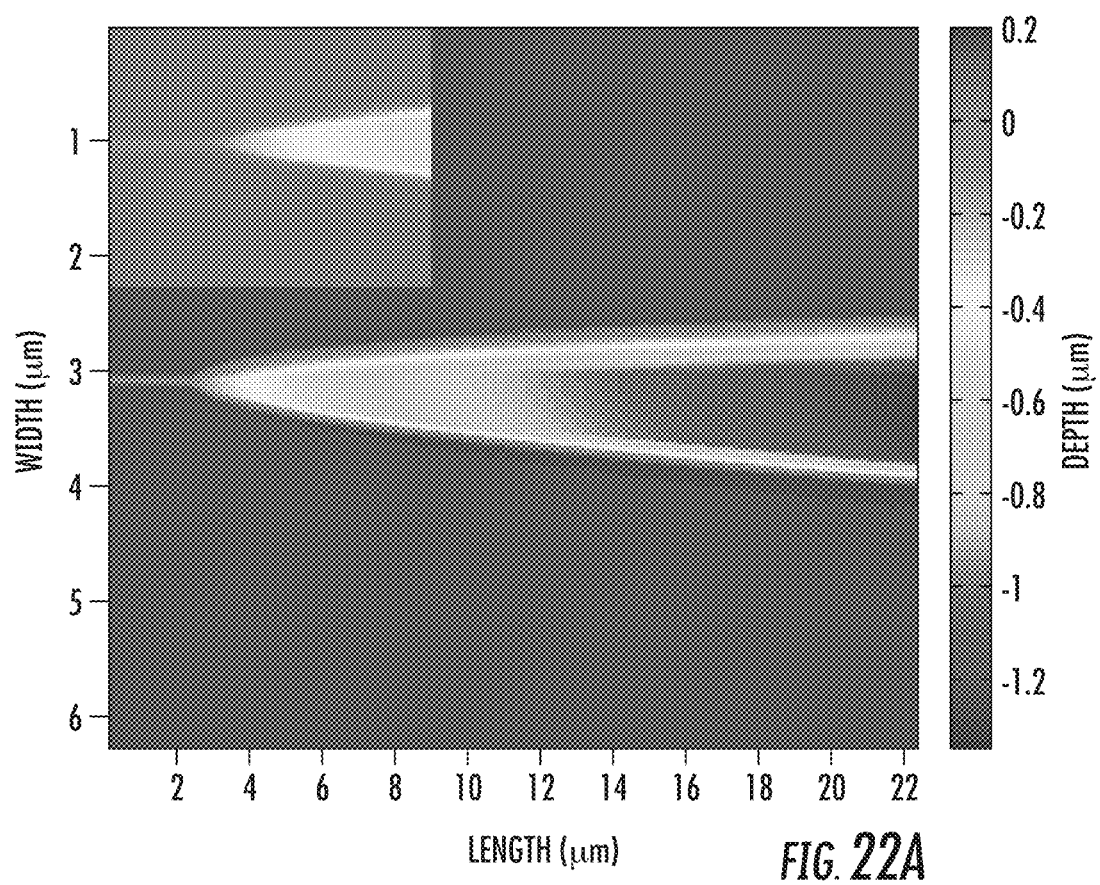
FIG. 22A is an atomic force microscopy image of a funnel interfaced to a nanochannel in which nanofunnel depth is measured at each position whose coordinates correspond to width and length according to embodiments of the present invention.
Figure 22B:
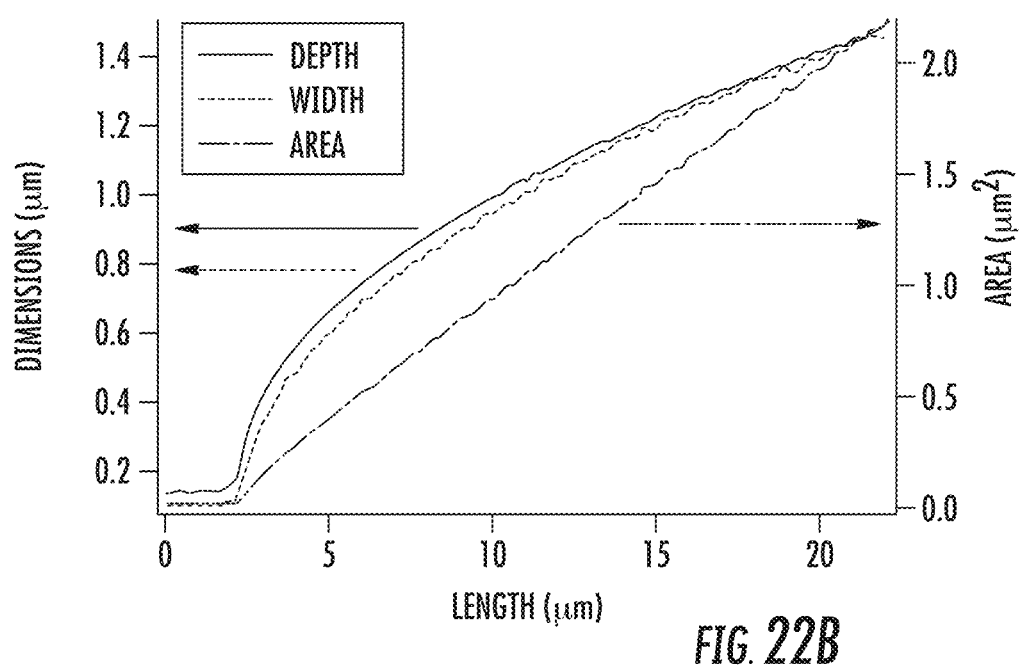
FIG. 22B is a graph of dimensions (depth, width and area) versus length according to embodiments of the present invention. The measurements of the funnel can be made using the image of FIG. 22A and the cross-sectional area of the funnel can vary linearly along its length.

In order to compare different funnel geometries in these experiments, and to compare experimental results to theoretical predictions, the electric field in the funnels and nanochannels can be compared. To determine these fields, the nanochannel and nanofunnel shape (width and depth) can be precisely determined using atomic force microscopy (FIGS. 22A, 22B), SEM imaging (FIGS. 3B, 3C, 7A, 7B, 7C, 23), and ion beam tomography, for example. The optimal shape(s) may change for macromolecules having different physical properties, systems with different polymer-solvent intermolecular interactions, and driving forces with different flow profiles, all parameters that can be investigated theoretically.

FIG. 23 illustrates a bitmap image 20bm used to create a corresponding FIB milled funnel 20 and nanochannel 30 (SEM image) with a length of about 22 μm and a graph of an AFM (Atomic Force microscopy) image of width (μm) versus length (μm).

Figure 24:
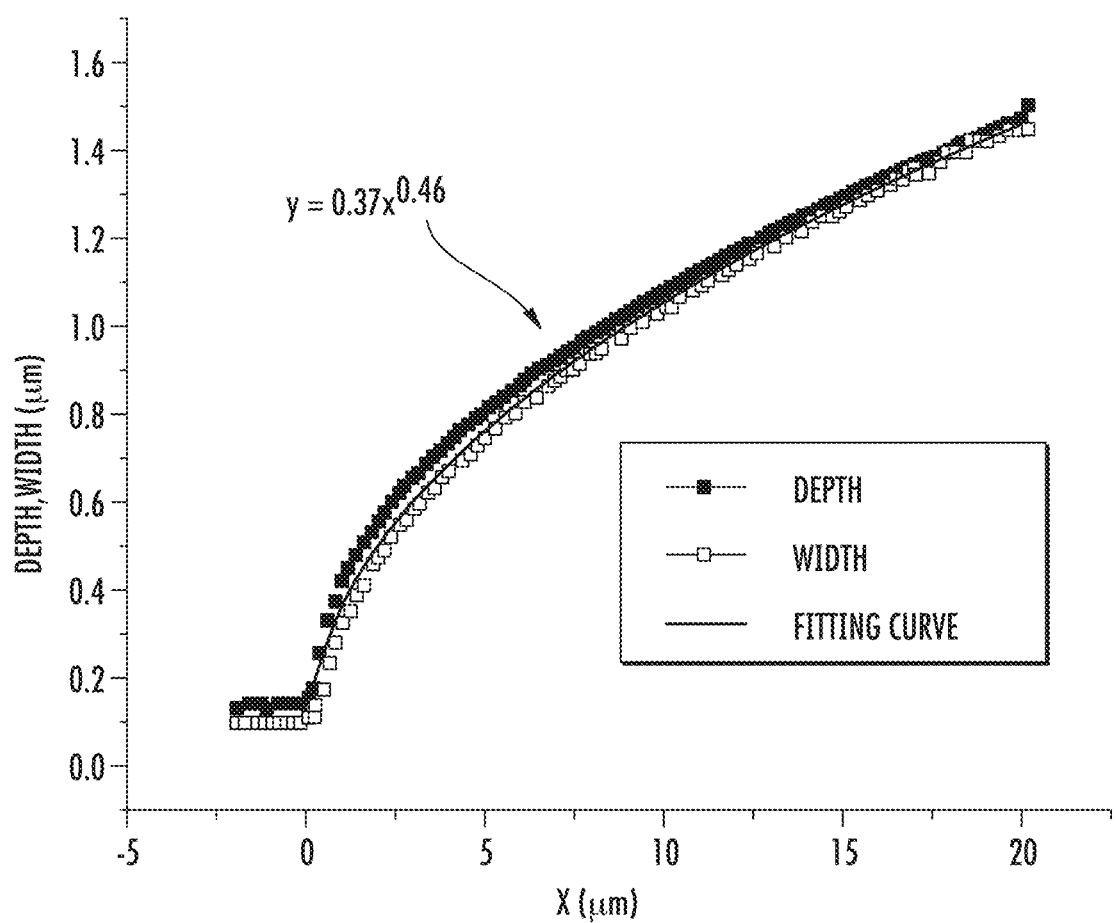
FIG. 24 is a graph of depth, width (μm) versus length x (μm) of exemplary funnel geometry according to embodiments of the present invention.

FIG. 24 is a graph showing a parabolic relationship of depth and width over a length of the nanofunnel 20 according to some embodiments of the present invention. That is, the nanofunnel(s) 20 can be configured to have both width and depth dimensions that vary in a parabolic, linear manner over its length according to some embodiments of the present invention.

Figure 25:
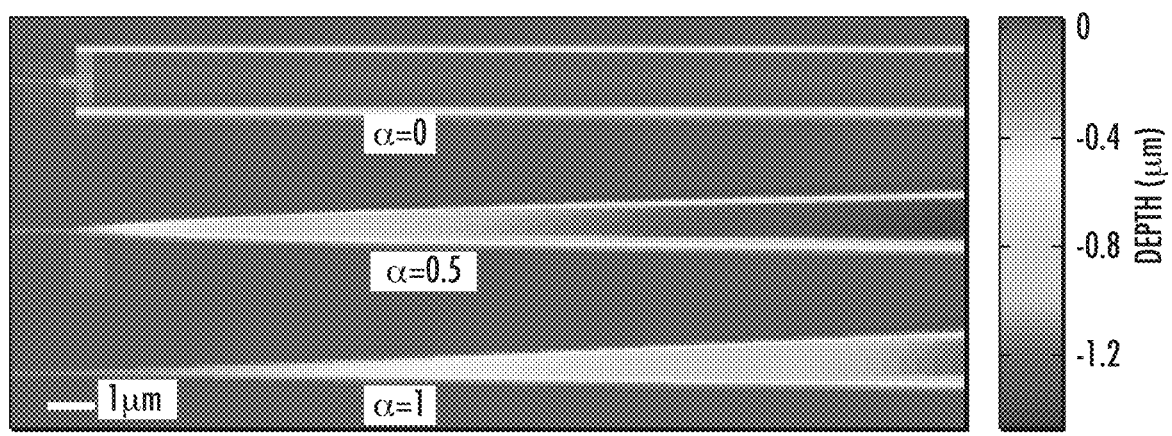
FIG. 25 is a set of AFM images for funnels having different values of a according to embodiments of the present invention.

FIG. 25 shows AFM images of nanofunnels defined by a power law function with a values of 0, 0.5, and 1. Devices incorporating such nanofunnels were used to determine the results represented in the table above. The gray or color scale labeled "Depth (μm)" on the right hand side of the figure shows how the intensities of the nanofunnel profiles on the left hand side of the figure correspond to nanofunnel depth.

Because these characterizations of nanofunnel dimensions provide an accurate determination of electric field strengths through the nanochannel/nanofunnel conduit, direct comparisons between experimental results and theoretical predictions can be made. FIG. 26A illustrates the comparison between the experimentally determined positions of the leading and tailing ends of a trapped λ-phage DNA molecule. FIG. 26B illustrates the comparison between the experimentally determined positions of the leading and tailing ends of a trapped T4-phage DNA molecule. FIG. 27 is a schematic illustration of an analysis system 100 which includes at least one device 10 with at least one nanofunnel 20, electrodes 70 and a control circuit 101 with a funnel applied voltage mode and a channel applied voltage mode, the funnel mode configured to apply a larger voltage than the channel mode.

FIG. 28 is a schematic illustration of a fabrication system 201 with a milling apparatus 200 and a circuit 200c with a nanofunnel patterning file 200f which can be totally onboard the apparatus 200, partially onboard the apparatus 200 or remote from the apparatus such as in one or more servers 225.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A device for processing one or more single molecules in fluid for analysis, comprising:
a nanofluidic chip comprising a substrate providing a plurality of nanofunnels, wherein each nanofunnel has a wide end and a narrow end and a length and varies in depth and width along the length, wherein the substrate also provides at least one microchannel, wherein the wide end of one or more nanofunnel of the plurality of nanofunnels merges into the at least one microchannel, wherein the at least one microchannel is sized and configured so that one or more single molecules in fluid is unconfined within the at least one microchannel, wherein the substrate further comprises a plurality of nanochannels, wherein the narrow end of each nanofunnel of the plurality of nanofunnels merges into an adjacently positioned associated one nanochannel of the plurality of nanochannels, and
wherein each of the plurality of nanofunnels has opposing sidewalls that face each other across the width, wherein each of the plurality of nanofunnels has an open upper surface in the substrate and a closed bottom surface between the sidewalls, and wherein the device further comprises a cover over the primary surface of the substrate to enclose the open upper surfaces of the plurality of nanofunnels to thereby provide a sealed nanofluidic device.

2. The device of claim 1, wherein the length of the nanofunnels extend along a plane of a primary surface of the substrate and the depth extends in a direction that is into the plane of the primary surface of the substrate, and wherein a length of the nanochannels and a length of the at least one microchannel extends along the plane of the primary surface of the substrate and a depth of each extends in a direction that is into the plane of the primary surface of the substrate.

3. The device of claim 2, wherein each of the plurality of nanofunnels is configured to fluidly receive a respective single molecule of DNA, protein, or other polymeric material as the one or more single molecules in fluid.

4. The device of claim 1, wherein the plurality of nanofunnels have width and depth dimensions that define the width and depth, respectively, and both the width and depth vary in a defined geometric relationship over substantially an entire length of the nanofunnel to alter a cross-sectional size of the nanofunnel by at least a factor of two from the wide end to the narrow end.

5. The device of claim 1, wherein the width and depth vary by about an order of magnitude or more from the wide end to the narrow end.

6. The device of claim 2, wherein at least some of the nanochannels have substantially constant width and depth dimensions, and wherein the narrow end of each nanofunnel of the plurality of nanofunnels have width and depth dimensions that substantially match the width and depth dimensions of the adjacently positioned associated nanochannel.

7. The device of claim 1, wherein the nanofunnels comprise at least a portion with a substantially parabolic contour.

8. The device of claim 1, wherein the nanofunnels comprise at least a portion with a substantially convex contour.

9. The device of claim 1, wherein the nanofunnels comprise at least a portion with a substantially concave contour.

10. The device of claim 1, wherein the nanofunnels have walls that angle inward at a constant slope.

11. The device of claim 1, wherein the nanofunnels have dimensions with an associated exponent "α" defined by a power law (width, depth~$x^α$), where x is an axial coordinate and alpha is a positive number.

12. The device of claim 1, wherein the nanofunnels have dimensions associated with a power law exponent α, where α is configured as a function of axial position x, such that $y \sim x^{α(x)}$.

13. The device of claim 1, further comprising a control circuit and a fluid transport system in communication with the nanofluidic chip for selectively transporting one or more single molecule in a fluid into and/or through one or more of the nanofunnels, wherein the control circuit is configured to direct the fluid transport system to trap a respective molecule or molecules in one or more of the plurality of nanofunnels.

14. The device of claim 1, further comprising a planar cover coupled to the substrate to define a sealed nanofluidic chip, wherein the substrate has a width dimension or a length dimension that extends in a direction corresponding to a direction of the width of each nanofunnel of the plurality of nanofunnels and that is coplanar with a plane of the primary surface, and wherein the plurality of nanofunnels are spaced apart from each other about the width dimension or the length dimension of the substrate.

15. The device of claim 2, wherein the narrow end of each nanofunnel of the plurality of nanofunnels defines an aspect ratio (AR) of depth:width that is about 10 or less.

16. A device for processing single molecules in fluid, comprising:
- a planar substrate providing a plurality of nanofunnels, wherein each nanofunnel has a wide end and a narrow end and a length and varies in depth and width along the length, wherein the substrate has a width dimension in a direction corresponding to the width or length of each nanofunnel, wherein the plurality of nanofunnels are spaced apart from each other about the width dimension of the substrate, and wherein the length of the nanofunnels extend along a plane of a primary surface of the planar substrate and the depth extends in a direction that is into the plane of the primary surface of the substrate;
- a plurality of nanochannels provided by the planar substrate, wherein the narrow end of each nanofunnel of the plurality of nanofunnels merges at an upstream or downstream location into an adjacently positioned associated one nanochannel of the plurality of nanochannels; and
- at least one microchannel that is also provided by the planar substrate, wherein the wide end of one or more nanofunnels of the plurality of nanofunnels merges into the at least one microchannel, and wherein the microchannel is sized and configured so that one or more single molecule in fluid is unconfined within the microchannel residing proximate the wide end of one or more of nanofunnels of the plurality of nanofunnels; and
- a cover coupled to the planar substrate over an open upper surface of the nanofunnels of the planar substrate to define a fluidic chip.

17. The device of claim 16, wherein the narrow end of each of the plurality of nanofunnels has an aspect ratio (AR) of depth:width that is about 10 or less.

18. A system for processing single molecules in fluid, comprising:
- a fluidic chip comprising a planar substrate and a cover coupled to the planar substrate; and
- a control circuit and a fluid transport system in communication with the nanofluidic chip,
- wherein the planar substrate comprises:
  - a plurality of nanofunnels, wherein each nanofunnel has a wide end and a narrow end and a length and varies in depth and width along the length, wherein the substrate has a width dimension in a direction corresponding to the width or length of each nanofunnel, wherein the plurality of nanofunnels are spaced apart from each other about the width dimension of the substrate, and wherein the length of the nanofunnels extend along a plane of a primary surface of the planar substrate and the depth extends in a direction that is into the plane of the primary surface of the substrate;
  - a plurality of nanochannels, wherein the narrow end of each nanofunnel of the plurality of nanofunnels merges at an upstream or downstream location into an adjacently positioned associated one nanochannel of the plurality of nanochannels; and
  - at least one microchannel, wherein the wide end of one or more nanofunnels of the plurality of nanofunnels merges into the at least one microchannel, and wherein the microchannel is sized and configured so that one or more single molecule in fluid is unconfined within the microchannel residing proximate the wide end of one or more of nanofunnels of the plurality of nanofunnels,
- wherein the cover resides over or under the primary surface of the planar substrate,
- wherein the control circuit and fluid transport system are configured to selectively transport one or more single molecule in a fluid into and/or through one or more of the plurality of nanofunnels, and wherein the control circuit is configured to direct the fluid transport system to trap a respective molecule or molecules in one or more of the plurality of nanofunnels.

* * * * *

UNITED STATES PATENT AND TRADEMARK OFFICE
CERTIFICATE OF CORRECTION

Page 1 of 1

PATENT NO. : 10,996,212 B2
APPLICATION NO. : 15/969267
DATED : May 4, 2021
INVENTOR(S) : Ramsey et al.

It is certified that error appears in the above-identified patent and that said Letters Patent is hereby corrected as shown below:

In the Specification

Column 2, Line 63: delete "1 to about 100 μm" insert -- 1 μm to about 100 μm --

Column 16, Line 52: delete "2-DNA" insert -- λ-DNA --

Column 17, Line 15: delete "k-DNA" insert -- λ-DNA --

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*